(12) United States Patent
Kolczewski et al.

(10) Patent No.: US 8,524,909 B2
(45) Date of Patent: Sep. 3, 2013

(54) TETRAHYDRO-PYRAN DERIVATIVES

(75) Inventors: Sabine Kolczewski, Loerrach (DE); Emmanuel Pinard, Linsdorf (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 435 days.

(21) Appl. No.: 13/010,864

(22) Filed: Jan. 21, 2011

(65) Prior Publication Data
US 2011/0190349 A1    Aug. 4, 2011

(30) Foreign Application Priority Data

Feb. 2, 2010 (EP) .................................... 10152359

(51) Int. Cl.
| | |
|---|---|
| C07D 401/04 | (2006.01) |
| C07D 209/52 | (2006.01) |
| C07D 405/04 | (2006.01) |
| C07D 309/14 | (2006.01) |
| A61K 31/4453 | (2006.01) |
| A61K 31/403 | (2006.01) |
| A61K 31/4025 | (2006.01) |
| A61K 31/351 | (2006.01) |

(52) U.S. Cl.
USPC ........... 546/207; 548/465; 548/517; 549/424; 514/326; 514/414; 514/422; 514/459

(58) Field of Classification Search
USPC ................. 549/424; 548/465, 517; 546/207; 514/326, 414, 422, 459
See application file for complete search history.

(56) References Cited

U.S. PATENT DOCUMENTS
4,598,089 A   7/1986   Hadvary et al.

FOREIGN PATENT DOCUMENTS
| EP | 0129748 | 5/2011 |
|---|---|---|
| WO | 2005/068463 | 7/2005 |
| WO | 2006/067423 | 6/2006 |
| WO | 2009/105509 | 8/2009 |

OTHER PUBLICATIONS

D'Andrea et al., Journal of Organic Chemistry vol. 56 (1991) pp. 3133-3137.
McNaught et al., IUPAC, Ed., Copedium Chem. Terminology 2nd Ed. 1997, XP002585005.
McNaught et al., IUPAC Ed., Copedium Chem. Terminology 2nd Ed. 1997, XP002585006.
Jacobson et al., Nature, vol. 179 (1957) pp. 633-634.
PCT International Search Report PCT/EP2011/051179—Issued: Jan. 28, 2011.

*Primary Examiner* — Bernard Dentz

(57) ABSTRACT

The present invention relates to a compound of formula I

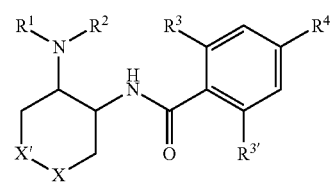

wherein $R^1/R^2$ are independently from each other hydrogen, $(CR_2)_o$-cycloalkyl, optionally substituted by lower alkyl or hydroxy, or are lower alkyl or heterocycloalkyl, and
o is 0 or 1; and
R may be the same or different and is hydrogen or lower alkyl; or
$R^1$ and $R^2$ may form together with the N atom to which they are attached a heterocycloalkyl group, selected from the group consisting of pyrrolidinyl, piperidinyl, 3-aza-bicyclo[3.1.0]hex-3-yl or 2-aza-bicyclo[3.1.0]hex-2-yl, which are optionally substituted by hydroxy;
$R^3$ is S-lower alkyl, lower alkyl, lower alkoxy or cycloalkyl;
$R^{3'}$ is hydrogen, lower alkyl substituted by halogen, lower alkyl or lower alkoxy
$R^4$ is lower alkyl substituted by halogen, lower alkyl or lower alkoxy;
X is —O— or —$CH_2$—;
X' is —O— or —$CH_2$—; with the proviso that one of X or X' is always —O— and the other is —$CH_2$—;
or to a pharmaceutically acceptable acid addition salt, to a racemic mixture, or to its corresponding enantiomer and/or optical isomer thereof.
It has been found that the compounds of formula I are good inhibitors of the glycine transporter 1 (GlyT-1) and therefore they may be used for the treatment of schizophrenia.

13 Claims, No Drawings

TETRAHYDRO-PYRAN DERIVATIVES

PRIORITY TO RELATED APPLICATION(S)

This application claims the benefit of European Patent Application No. 10152359.5, filed Feb. 2, 2010, which is hereby incorporated by reference in its entirety.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, Neuron, 2000, 28:325-33). For decades research has focused on the "dopaminergic hyperactivity" hypothesis which has led to therapeutic interventions involving blockade of the dopaminergic system (Vandenberg R J and Aubrey K R., Exp. Opin. Ther. Targets, 2001, 5(4): 507-518; Nakazato A and Okuyama S, et al., 2000, Exp. Opin. Ther. Patents, 10(1): 75-98). This pharmacological approach poorly address negative and cognitive symptoms which are the best predictors of functional outcome (Sharma T., Br. J. Psychiatry, 1999, 174(suppl. 28): 44-51).

A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly in healthy volunteers, PCP-induced psychotomimetic action incorporates positive and negative symptoms as well as cognitive dysfunction, thus closely resembling schizophrenia in patients (Javitt D C et al., 1999, Biol. Psychiatry, 45: 668-679 and refs. herein). Furthermore transgenic mice expressing reduced levels of the NMDAR1 subunit displays behavioral abnormalities similar to those observed in pharmacologically induced models of schizophrenia, supporting a model in which reduced NMDA receptor activity results in schizophrenia-like behavior (Mohn A R et al., 1999, Cell, 98: 427-236).

Glutamate neurotransmission, in particular NMDA receptor activity, plays a critical role in synaptic plasticity, learning and memory, such as the NMDA receptors appears to serve as a graded switch for gating the threshold of synaptic plasticity and memory formation (Hebb D O, 1949, The organization of behavior, Wiley, NY; Bliss TV and Collingridge G L, 1993, Nature, 361: 31-39). Transgenic mice overexpressing the NMDA NR2B subunit exhibit enhanced synaptic plasticity and superior ability in learning and memory (Tang J P et al., 1999, Nature: 401-63-69).

Thus, if a glutamate deficit is implicate in the pathophysiology of schizophrenia, enhancing glutamate transmission, in particular via NMDA receptor activation, would be predicted to produce both anti-psychotic and cognitive enhancing effects.

The amino acid glycine is known to have at least two important functions in the CNS. It acts as an inhibitory amino acid, binding to strychnine sensitive glycine receptors, and it also influences excitatory activity, acting as an essential co-agonist with glutamate for N-methyl-D-aspartate (NMDA) receptor function. While glutamate is released in an activity-dependent manner from synaptic terminals, glycine is apparently present at a more constant level and seems to modulate/control the receptor for its response to glutamate.

One of the most effective ways to control synaptic concentrations of neurotransmitter is to influence their re-uptake at the synapses. Neurotransmitter transporters by removing neurotransmitters from the extracellular space, can control their extracellular lifetime and thereby modulate the magnitude of the synaptic transmission (Gainetdinov R R et al, 2002, Trends in Pharm. Sci., 23(8): 367-373).

Glycine transporters, which form part of the sodium and chloride family of neurotransmitter transporters, play an important role in the termination of post-synaptic glycinergic actions and maintenance of low extracellular glycine concentration by re-uptake of glycine into presynaptic nerve terminals and surrounding fine glial processes.

Two distinct glycine transporter genes have been cloned (GlyT-1 and GlyT-2) from mammalian brain, which give rise to two transporters with ~50% amino acid sequence homology. GlyT-1 presents four isoforms arising from alternative splicing and alternative promoter usage (1a, 1b, 1c and 1d). Only two of these isoforms have been found in rodent brain (GlyT-1a and GlyT-1b). GlyT-2 also presents some degree of heterogeneity. Two GlyT-2 isoforms (2a and 2b) have been identified in rodent brains. GlyT-1 is known to be located in CNS and in peripheral tissues, whereas GlyT-2 is specific to the CNS. GlyT-1 has a predominantly glial distribution and is found not only in areas corresponding to strychnine sensitive glycine receptors but also outside these areas, where it has been postulated to be involved in modulation of NMDA receptor function (Lopez-Corcuera B et al., 2001, Mol. Mem. Biol., 18: 13-20). Thus, one strategy to enhance NMDA receptor activity is to elevate the glycine concentration in the local microenvironment of synaptic NMDA receptors by inhibition of GlyT-1 transporter (Bergereon R. Et al., 1998, Proc. Natl. Acad. Sci. USA, 95: 15730-15734; Chen L et al., 2003, J. Neurophysiol., 89 (2): 691-703).

Glycine transporters inhibitors are suitable for the treatment of neurological and neuropsychiatric disorders. The majority of diseases states implicated are psychoses, schizophrenia (Armer R E and Miller D J, 2001, Exp. Opin. Ther. Patents, 11 (4): 563-572), psychotic mood disorders such as severe major depressive disorder, mood disorders associated with psychotic disorders such as acute mania or depression associated with bipolar disorders and mood disorders associated with schizophrenia, (Pralong E T et al., 2002, Prog. Neurobiol., 67: 173-202), autistic disorders (Carlsson M L, 1998, J. Neural Transm. 105: 525-535), cognitive disorders such as dementias, including age related dementia and senile dementia of the Alzheimer type, memory disorders in a mammal, including a human, attention deficit disorders and pain (Armer R E and Miller D J, 2001, Exp. Opin. Ther. Patents, 11 (4): 563-572).

Thus, increasing activation of NMDA receptors via GlyT-1 inhibition may lead to agents that treat psychosis, schizophrenia, dementia and other diseases in which cognitive processes are impaired, such as attention deficit disorders or Alzheimer's disease.

SUMMARY OF THE INVENTION

The present invention provides a compound of formula I

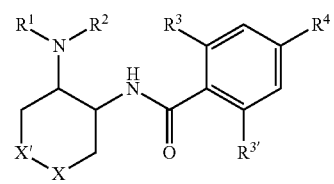

wherein
R¹ and R² are each independently hydrogen, (CR₂)ₒ-cycloalkyl optionally substituted by lower alkyl or hydroxy, or are lower alkyl or heterocycloalkyl,
  o is 0 or 1; and
  each R is the same or different and is hydrogen or lower alkyl; or
R¹ and R² together with the N atom to which they are attached form a heterocycloalkyl group, selected from the group consisting of pyrrolidinyl, piperidinyl, 3-aza-bicyclo[3.1.0]hex-3-yl and 2-aza-bicyclo[3.1.0]hex-2-yl, each of which is optionally substituted by hydroxy;
R³ is S-lower alkyl, lower alkyl, lower alkoxy or cycloalkyl;
R³' is hydrogen, lower alkyl substituted by halogen, lower alkyl or lower alkoxy;
R⁴ is lower alkyl substituted by halogen, lower alkyl or lower alkoxy;
X is —O— or —CH—; and
X' is —O— or —CH—; with the proviso that one of X or X' is always —O— and the other is —CH₂—;
or a pharmaceutically acceptable acid addition salt, a racemic mixture, or a corresponding enantiomer and/or optical isomer thereof.

Furthermore, the invention includes all racemic mixtures, all their corresponding enantiomers and/or optical isomers.

The present invention provides compounds of formula I per se and pharmaceutical compositions containing them. The invention further provides methods for the manufacture of the compounds and compositions of the invention.

Furthermore, the present invention relates to pharmaceutical compositions containing the compounds of formula I and to their use in the treatment of neurological and neuropsychiatric disorders.

Compounds of formula I are good inhibitors of the glycine transporter 1 (GlyT-1), and that they have a good selectivity to glycine transporter 2 (GlyT-2) inhibitors. Thus, the invention provides methods for the treatment of diseases related to activation of NMDA receptors via Glyt-1 inhibition, in particular neurological and neuropsychiatric disorders. The invention provides methods for the treatment of illnesses such as psychoses, dysfunction in memory and learning, schizophrenia, dementia and other diseases in which cognitive processes are impaired, such as attention deficit disorders or Alzheimer's disease.

The preferred indications using the compounds of the present invention are schizophrenia, cognitive impairment and Alzheimer's disease.

DETAILED DESCRIPTION OF THE INVENTION

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a lower alkyl group as defined above, which is linked to the molecule through an O atom.

The term "cycloalkyl" denotes a saturated or partially saturated ring containing from 3 to 7 carbon atoms, for example cyclopropyl, cyclobutyl, cyclopentyl, cyclopentenyl, cyclohexyl, cyclohexenyl, cycloheptyl or cycloheptenyl. Preferred cycloalkyl rings are cyclopropyl and cyclopentyl.

The term "heterocycloalkyl" denotes a saturated or partially saturated ring containing from 3 to 6 ring atoms, wherein at least one ring atom is a heteroatom selected from N, S and O and the remaining ring atoms are C, for example piperazinyl, pyrrolidinyl, oxetanyl, morpholinyl, piperidinyl, and tetrahydropyranyl.

The term "halogen" denotes chlorine, iodine, fluorine and bromine.

The term "lower alkyl substituted by halogen" denotes a lower alkyl group as defined above, wherein at least one hydrogen atom is replaced by a halogen atom, for example the following groups: CF₃, CHF₂, CH₂F, CH₂CF₃, CH₂CHF₂, CH₂CH₂F, CH₂CH₂CF₃, CH₂CH₂CH₂CF₃, CH₂CH₂Cl, CH₂CF₂CF₃, CH₂CF₂CHF₂, CF₂CHFCF₃, C(CH₃)₂CF₃, CH(CH₃)CF₃ or CH(CH₂F)CH₂F.

The term "pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The term "therapeutically effective amount" means an amount that is effective to prevent, alleviate or ameliorate symptoms of disease or prolong the survival of the subject being treated.

One embodiment of the invention provides compounds of formula I, wherein X is O and X' is CH₂, which have the following structure:

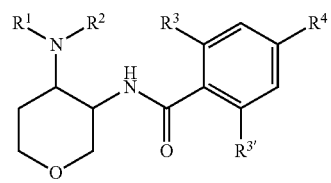

I-1 wherein
R¹ and R² are each independently from each other hydrogen, (CR₂)ₒ-cycloalkyl optionally substituted by lower alkyl or hydroxy, or are lower alkyl or heterocycloalkyl,
  o is 0 or 1; and
  each R is the same or different and is hydrogen or lower alkyl; or
R¹ and R² together with the N atom to which they are attached form a heterocycloalkyl group, selected from the group consisting of pyrrolidinyl, piperidinyl, 3-aza-bicyclo[3.1.0]hex-3-yl and 2-aza-bicyclo[3.1.0]hex-2-yl, each of which is optionally substituted by hydroxy;
R³ is S-lower alkyl, lower alkyl, lower alkoxy or cycloalkyl;
R³' is hydrogen, lower alkyl substituted by halogen, lower alkyl or lower alkoxy; and
R⁴ is lower alkyl substituted by halogen, lower alkyl or lower alkoxy;
or a pharmaceutically acceptable acid addition salt, a racemic mixture, or its corresponding enantiomer and/or optical isomer thereof.

One embodiment from this group are compounds, wherein R¹ and R² together with the N atom to which they are attached form a heterocycloalkyl group, selected from the group consisting of pyrrolidinyl, piperidinyl, 3-aza-bicyclo[3.1.0]hex-3-yl and 2-aza-bicyclo[3.1.0]hex-2-yl, each of which is optionally substituted by hydroxy, for example the following compounds:

2-methoxy-6-methylsulfanyl-N-((3RS,4SR)-4-pyrrolidin-1-yl-tetrahydro-pyran-3-yl)-4-trifluoromethyl-benzamide;
(−)-2-methoxy-6-methylsulfanyl-N-(4-pyrrolidin-1-yl-tetrahydro-pyran-3-yl)-4-trifluoromethyl-benzamide;
2-cyclopropyl-N-((3SR,4RS)-4-pyrrolidin-1-yl-tetrahydro-pyran-3-yl)-4-trifluoromethyl-benzamide;
2-methylsulfanyl-N-((3SR,4RS)-4-pyrrolidin-1-yl-tetrahydro-pyran-3-yl)-4,6-bis-trifluoromethyl-benzamide;
2-methyl-N-((3SR,4RS)-4-pyrrolidin-1-yl-tetrahydro-pyran-3-yl)-4,6-bis-trifluoromethyl-benzamide;
2-cyclopropyl-N-((3SR,4RS)-4-pyrrolidin-1-yl-tetrahydro-pyran-3-yl)-4,6-bis-trifluoromethyl-benzamide;
2-cyclopropyl-N-((3SR,4RS)-4-piperidin-1-yl-tetrahydro-pyran-3-yl)-4-trifluoromethyl-benzamide;
2,6-dimethyl-N-((3SR,4RS)-4-pyrrolidin-1-yl-tetrahydro-pyran-3-yl)-4-trifluoromethyl-benzamide;
2,6-diethyl-N-((3SR,4RS)-4-pyrrolidin-1-yl-tetrahydro-pyran-3-yl)-4-trifluoromethyl-benzamide;
2-ethyl-6-methoxy-N-((3SR,4RS)-4-pyrrolidin-1-yl-tetrahydro-pyran-3-yl)-4-trifluoromethyl-benzamide;
2-ethyl-6-methyl-N-((3SR,4RS)-4-pyrrolidin-1-yl-tetrahydro-pyran-3-yl)-4-trifluoromethyl-benzamide;
2-cyclopropyl-6-methoxy-N-((3SR,4RS)-4-pyrrolidin-1-yl-tetrahydro-pyran-3-yl)-4-trifluoromethyl-benzamide;
N-[(3S,4R)-4-(3-aza-bicyclo[3.1.0]hex-3-yl)-tetrahydro-pyran-3-yl]-2-cyclopropyl-4-trifluoromethyl-benzamide;
(+)-2-cyclopropyl-N-(4-pyrrolidin-1-yl-tetrahydro-pyran-3-yl)-4-trifluoromethyl-benzamide;
(−)-2-cyclopropyl-N-(4-pyrrolidin-1-yl-tetrahydro-pyran-3-yl)-4-trifluoromethyl-benzamide;
(+)-2-methyl-N-trans-(4-pyrrolidin-1-yl-tetrahydro-pyran-3-yl)-4,6-bis-trifluoromethyl-benzamide;
(−)-2-methyl-N-trans-(4-pyrrolidin-1-yl-tetrahydro-pyran-3-yl)-4,6-bis-trifluoromethyl-benzamide;
(+)-2-methylsulfanyl-N-trans-(4-pyrrolidin-1-yl-tetrahydro-pyran-3-yl)-4,6-bis-trifluoromethyl-benzamide;
(−)-2-methylsulfanyl-N-trans-(4-pyrrolidin-1-yl-tetrahydro-pyran-3-yl)-4,6-bis-trifluoromethyl-benzamide;
(+)-2-cyclopropyl-N-(4-pyrrolidin-1-yl-tetrahydro-pyran-3-yl)-4,6-bis-trifluoromethyl-benzamide;
(−)-2-cyclopropyl-N-(4-pyrrolidin-1-yl-tetrahydro-pyran-3-yl)-4,6-bis-trifluoromethyl-benzamide;
(+)-2,6-dimethyl-N-4-pyrrolidin-1-yl-tetrahydro-pyran-3-yl)-4-trifluoromethyl-benzamide;
(−)-2,6-Dimethyl-N-4-pyrrolidin-1-yl-tetrahydro-pyran-3-yl)-4-trifluoromethyl-benzamide;
(+)-2-methoxy-6-methyl-N-(4-pyrrolidin-1-yl-tetrahydro-pyran-3-yl)-4-trifluoromethyl-benzamide;
(−)-2-methoxy-6-methyl-N-4-pyrrolidin-1-yl-tetrahydro-pyran-3-yl)-4-trifluoromethyl-benzamide;
(+)-2-ethyl-6-methoxy-N-4-pyrrolidin-1-yl-tetrahydro-pyran-3-yl)-4-trifluoromethyl-benzamide;
(+2-ethyl-6-methoxy-N-(4-pyrrolidin-1-yl-tetrahydro-pyran-3-yl)-4-trifluoromethyl-benzamide;
(+)-2-cyclopropyl-6-methoxy-N-4-pyrrolidin-1-yl-tetrahydro-pyran-3-yl)-4-trifluoromethyl-benzamide;
(+2-cyclopropyl-6-methoxy-N-(4-pyrrolidin-1-yl-tetrahydro-pyran-3-yl)-4-trifluoromethyl-benzamide; and
N-(3SR,4RS)-4-(2-aza-bicyclo[3.1.0]hex-2-yl)-tetrahydro-pyran-3-yl]-2-methoxy-6-methylsulfanyl-4-trifluoromethyl-benzamide.

A further embodiment from this group are compounds wherein $R^1$ and $R^2$ are each independently hydrogen or $(CR_2)_o$-cycloalkyl, o is 0 or 1; and each R is the same or different and is hydrogen or lower alkyl, for example
N-((3SR,4RS)-4-cyclopentylamino-tetrahydro-pyran-3-yl)-2-cyclopropyl-4-trifluoromethyl-benzamide;
2-cyclopropyl-N-[(3RS,4SR)-4-(1-cyclopropyl-ethylamino)-tetrahydro-pyran-3-yl]-4-trifluoromethyl-benzamide;
(+)-N-(trans-4-cyclopentylamino-tetrahydro-pyran-3-yl)-2-cyclopropyl-4-trifluoromethyl-benzamide; and
(+)-N-4-cyclohexylamino-tetrahydro-pyran-3-yl)-2-cyclopropyl-4-trifluoromethyl-benzamide.

Another embodiment of the invention provides compounds of formula I, wherein X is $CH_2$ and X' is O having the following structure

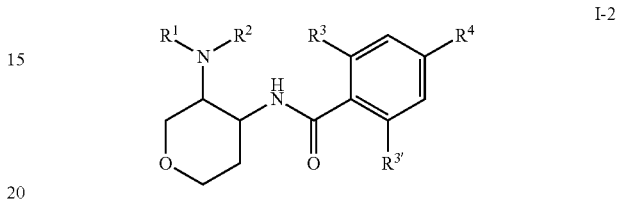

I-2 wherein
$R^1$ and $R^2$ are each independently hydrogen, $(CR_2)_o$-cycloalkyl optionally substituted by lower alkyl or hydroxy, or are lower alkyl or heterocycloalkyl,
o is 0 or 1; and
each R is the same or different and is hydrogen or lower alkyl; or
$R^1$ and $R^2$ together with the N atom to which they are attached form a heterocycloalkyl group, selected from the group consisting of pyrrolidinyl, piperidinyl, 3-aza-bicyclo[3.1.0]hex-3-yl and 2-aza-bicyclo[3.1.0]hex-2-yl, each of which is optionally substituted by hydroxy;
$R^3$ is S-lower alkyl, lower alkyl, lower alkoxy or cycloalkyl;
$R^{3'}$ is hydrogen, lower alkyl substituted by halogen, lower alkyl or lower alkoxy;
$R^4$ is lower alkyl substituted by halogen, lower alkyl or lower alkoxy;
or a pharmaceutically acceptable acid addition salt, a racemic mixture, or its corresponding enantiomer and/or optical isomer thereof, for example the following compounds
cis-2-methoxy-6-methylsulfanyl-N-(3-pyrrolidin-1-yl-tetrahydro-pyran-4-yl)-4-trifluoromethyl-benzamide;
(−)-2-methoxy-6-methylsulfanyl-N-(3-pyrrolidin-1-yl-tetrahydro-pyran-4-yl)-4-trifluoromethyl-benzamide; and
(+)-2-methoxy-6-methylsulfanyl-N-(3-pyrrolidin-1-yl-tetrahydro-pyran-4-yl)-4-trifluoromethyl-benzamide.

The present compounds of formula I and their pharmaceutically acceptable salts can be prepared by methods known in the art, for example, by processes described below, which process comprises
a) reacting a compound of formula

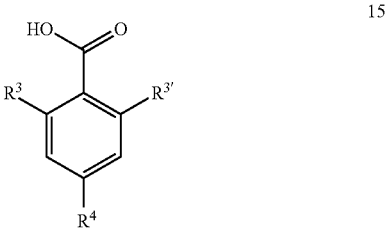

15 with a compound of formula

[Structure 10-1: piperidine/tetrahydropyran ring with R¹R²N- and -NH₂ substituents, X and X' ring atoms]

in the presence of an activating agent such as HATU (o-(7-azabenzotriazol-1-yl)-1,1,3,3-tetramethyluronium hexafluorophosphate)
to obtain a compound of formula

[Structure I: ring with R¹R²N- group and -NHC(O)-aryl group with R³, R³', R⁴ substituents]

wherein the substituents are as defined above, or
  b) reductively aminating a compound of formula

[Structure 3: tetrahydropyran-4-one with 3-NHC(O)-aryl substituent bearing R³, R³', R⁴]

with a compound of formula

NHR¹R² and separating the compound obtained by column chromatography to obtain compounds of formulas

[Structure I-1 cis]

and

[Structure I-1 trans]

wherein the substituents are as defined above, or
  c) alkylating or reductively aminating a compound of formula

[Structure 27: tetrahydropyran ring with NH₂ and -NHC(O)-aryl group bearing R³, R³', R⁴]

to obtain a compound of formula

[Structure I-2: tetrahydropyran with R¹R²N- and -NHC(O)-aryl group bearing R³, R³', R⁴]

wherein the substituents are as defined above, and,
if desired, converting the compounds obtained into pharmaceutically acceptable acid addition salts.

The compounds of formula I can be prepared in accordance with process variant a) or b) or c) and with the following schemes 1-7. The starting material is commercially available or can be prepared in accordance with known methods.

General Synthesis

Scheme 1

[Compound 1: dioxolane-protected tetrahydropyranone with NH₂]

→

[Compound 2: dioxolane-protected ring with -NHC(O)-aryl(R³,R³',R⁴)]

→

[Compound 3: tetrahydropyran-4-one with -NHC(O)-aryl(R³,R³',R⁴)]

→

[Compound I-1 cis: R¹R²N- tetrahydropyran with -NHC(O)-aryl(R³,R³',R⁴)]

+

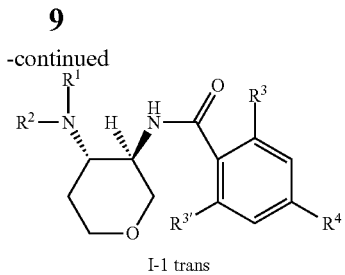

I-1 trans

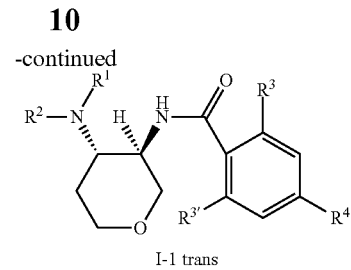

I-1 trans 1,4,8-Trioxaspiro[4,5]decan-6-amine (CAS 1068523-26-1) 1 was coupled with an acid using the coupling agent O-(7-azabenzotriazol-1-yl)-N,N,N',N'-tetramethyluronium hexafluorophosphate (=HATU) in dimethylformamide to obtain amide 2. The protecting group was cleaved with HCl to yield ketone 3. Reductive amination yielded a mixture of I-1 cis and I-1 trans which was separated by column chromatography.

3,6-Dihydro-2H-pyran 4 was reacted with N,N-dibromocarbamic acid tert butylester (CAS 358365-86-3) to intermediate 5 which was treated with sodium hydride to yield aziridine 6. Ring opening with sodium azide gave the trans-configurated azide 7 which was reduced with hydrogen and a platinum catalyst to amine 8. Alkylation or reductive amination gave amine 9. Cleavage of the Boc-protecting group was achieved with HCl to yield diamine 10 which was coupled with an acid using the coupling agent O-(7-azabenzotriazol-1-yl)-N,N,N',N'-tetramethyluronium hexafluorophosphate (=HATU) in dimethylformamide to obtain amide I-1 trans.

Scheme 2

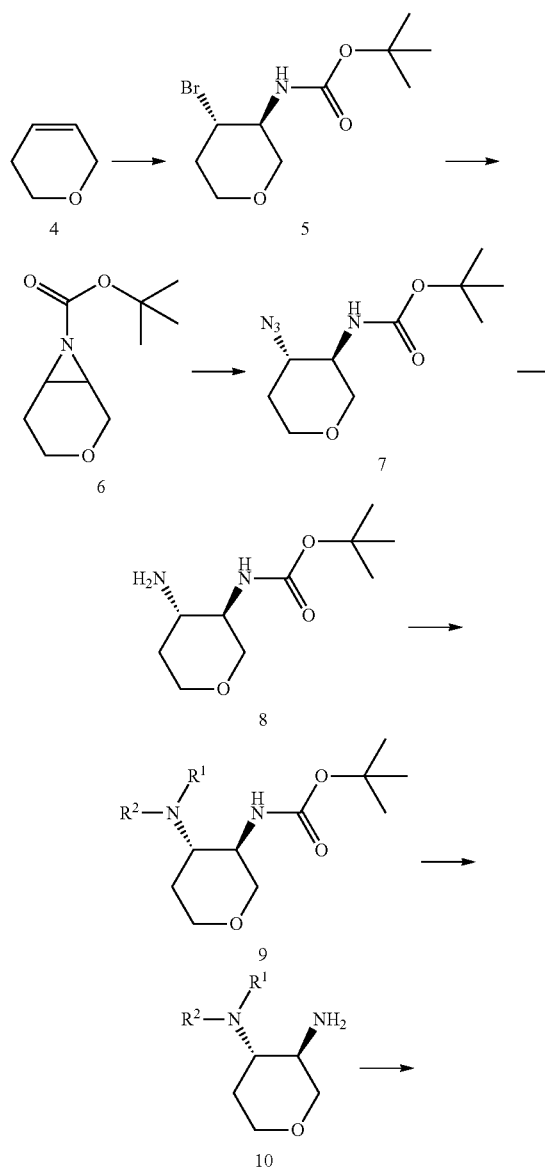

Scheme 3

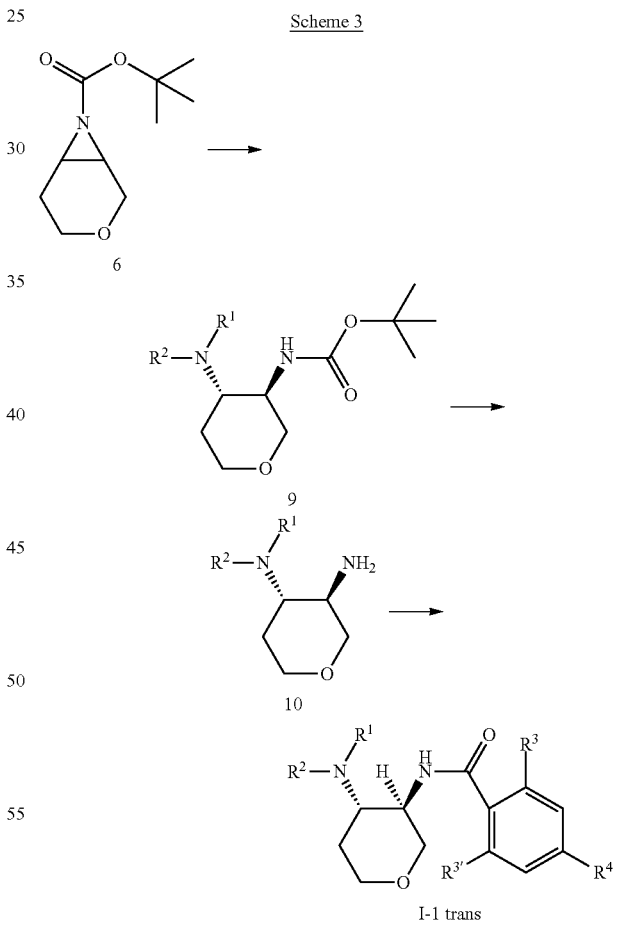

Aziridine 6 was treated with the amine R¹R²NH to provide trans amine 9. Cleavage of the Boc-protecting group was achieved with HCl to yield diamine 10 which was coupled with an acid using the coupling agent O-(7-azabenzotriazol-1-yl)-N,N,N',N'-tetramethyluronium hexafluorophosphate (=HATU) in dimethylformamide to obtain amide I-1 trans.

Scheme 4

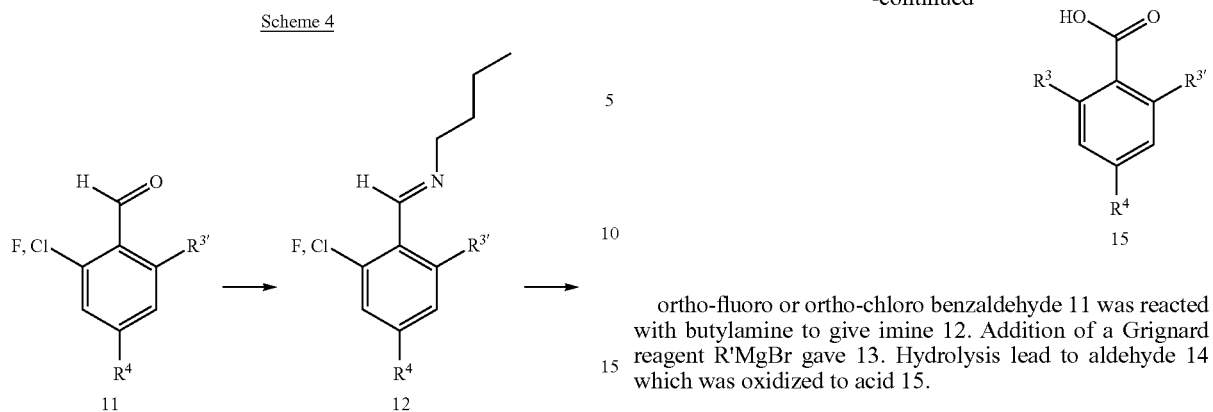

ortho-fluoro or ortho-chloro benzaldehyde 11 was reacted with butylamine to give imine 12. Addition of a Grignard reagent R'MgBr gave 13. Hydrolysis lead to aldehyde 14 which was oxidized to acid 15.

Scheme 5

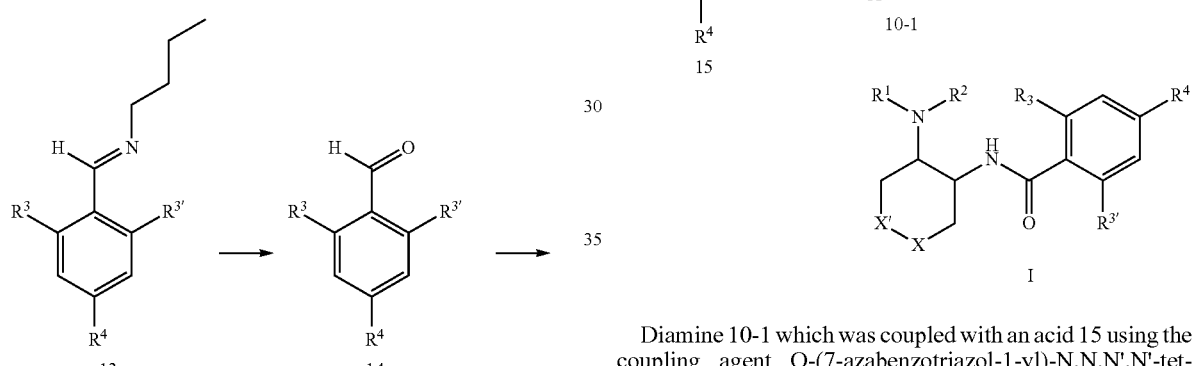

Diamine 10-1 which was coupled with an acid 15 using the coupling agent O-(7-azabenzotriazol-1-yl)-N,N,N',N'-tetramethyluronium hexafluorophosphate (=HATU) in dimethylformamide to obtain amide I.

Scheme 6

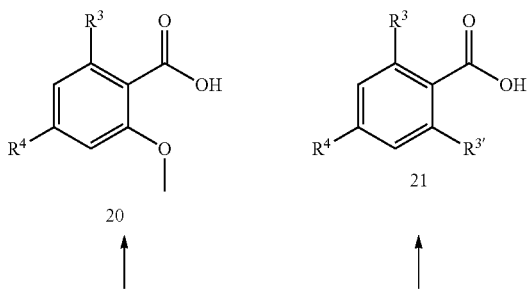

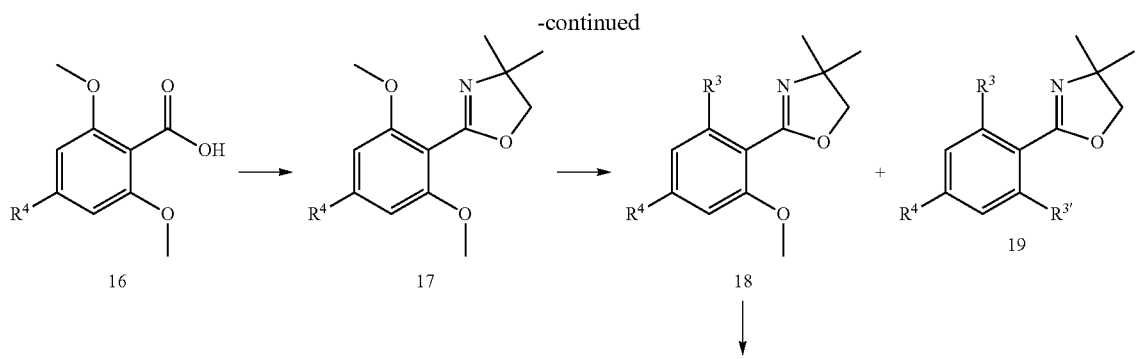

The substituents are as described above and $R^3$ and $R^{3'}$ are different from lower alkoxy. Some ortho-ortho' substituted acids are prepared according to scheme 6 following methodology described by A. I. Meyers et al. *JOC*, 1978, 43, 1372. Ortho-ortho' methoxy acid derivative 16 is first converted to the oxazolidinone 17 which is treated with a Grignard reagent $R^3MgX$ to provide intermediate 18 (resulting from a mono addition of $R^3MgX$) and intermediate 19 (resulting from an addition of $R^{3'}MgX$) which are then hydrolyzed to respectively acids 20 and 21. Intermediate 18 can also be reacted with a different Grignard reagent $R^{3'}MgX$ to provide intermediate 22 which is then hydrolyzed to acid 23.

Scheme 7

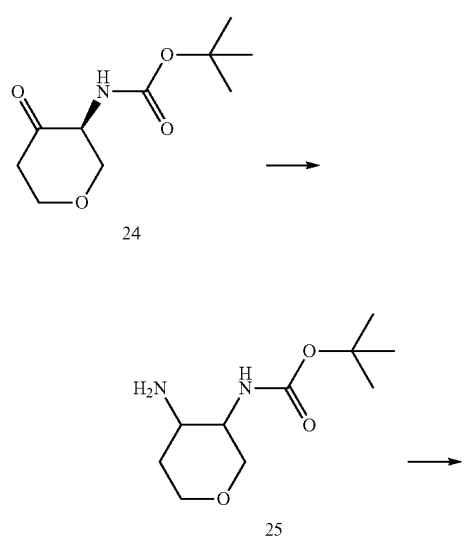

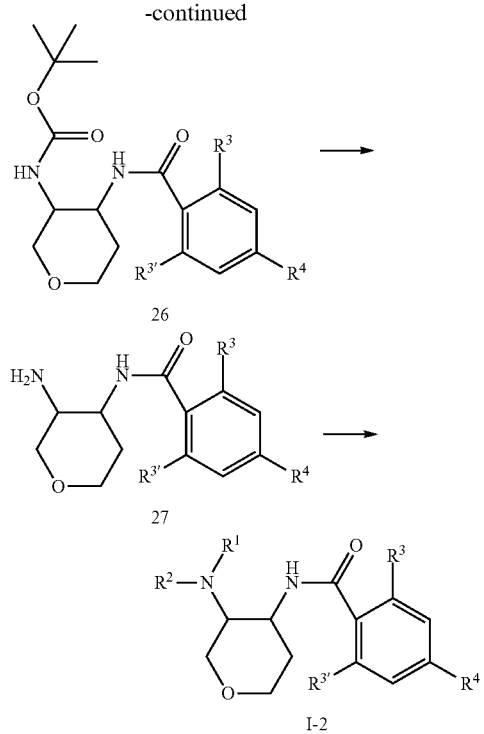

Ketone 24 (CAS 477584-38-6) is reductively aminated to give a mixture of cis- and trans-25 which was coupled with an acid using the coupling agent O-(7-azabenzotriazol-1-yl)-N,N,N',N'-tetramethyluronium hexafluorophosphate (=HATU) in dimethylformamide to obtain amide cis- and trans-26.

Cleavage of the Boc-protecting group and subsequent alkylation or reductive amination gave the final compound I-2 as a mixture of cis and trans.

SYNTHESIS OF INTERMEDIATES

Intermediate A

2-Methoxy-6-methylsulfanyl-4-trifluoromethyl-benzoic acid

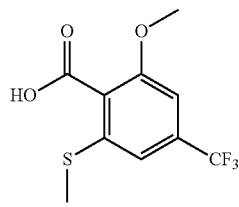

N,N,N'N'-Tetramethylethylendiamine (21 g, 177 mmol) was added drop-wise at −70° C. to a solution of sec-butyllithium (110 mL, 1.4 M in cyclohexane, 154 mmol) in 180 mL tetrahydrofuran. 2-Methoxy-4-trifluoromethyl-benzoic acid (13 g, 59 mmol) in 60 mL tetrahydrofuran was added drop-wise at −70° C. over 2 hours. After complete addition stirring was continued at −70° C. for another 2 hours. Dimethyl disulfide (20 g, 207 mmol) was added at −70° C. within 10 min. Stirring was continued at −70° C. for another hour and the reaction was allowed to warm up. The reaction mixture was quenched with 150 mL water and extracted with 200 mL ethyl acetate. The aqueous phase was adjusted to pH1 by addition of 25% HCl and extracted twice with dichloromethane. The combined organic phases were dried on sodium sulfate, filtered and evaporated. The crude product was crystallized with heptane and yielded the title compound as a white solid (1.75 g, 11%), MS: m/e=265.1 [(M−H)⁻].

Intermediate B

2-Methoxy-6-methylsulfanyl-4-trifluoromethyl-N-(1,4,8-trioxa-spiro[4.5]dec-6-yl)-benzamide

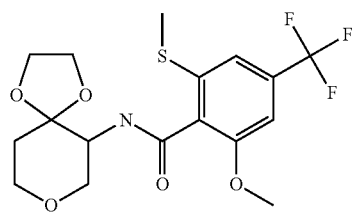 [SMILES: COc1cc(C(F)(F)F)cc(SC)c1C(=O)NC1COCCC12OCCO2]

2-Methoxy-6-methylsulfanyl-4-trifluoromethyl-benzoic acid (intermediate A, 400 mg, 1.5 mmol) was dissolved in 10 mL dimethylformamide. N,N-Diisopropyl ethyl amine (505 mg, 3.9 mmol) and O-(7-azabenzotriazol-1-yl)-N,N,N',N'-tetramethyluronium hexafluorophosphate (571 mg, 1.5 mmol) were added. After 10 minutes of stirring at room temperature 1,4,8-trioxaspiro[4,5]decan-6-amine (CAS 1068523-26-1) (359 mg, 2.2 mmol) was added. The reaction mixture was stirred at room temperature overnight. The solvent was evaporated off. The residue was taken up in 2N sodium carbonate solution and ethyl acetate and was extracted three times with ethyl acetate. The combined organic phases were dried on sodium sulfate, filtered and evaporated. Purification of the residue by flash chromatography on silica gel (heptane/ethyl acetate/triethylamine 1:0:0→10:10:1) yielded 2-methoxy-6-methylsulfanyl-4-trifluoromethyl-N-(1,4,8-trioxa-spiro[4.5]dec-6-yl)-benzamide as a white solid (462 mg, 75%), MS: m/e=408.2 [(M+H)⁺].

Intermediate C

2-Methoxy-6-methylsulfanyl-N-(4-oxo-tetrahydro-pyran-3-yl)-4-trifluoromethyl-benzamide

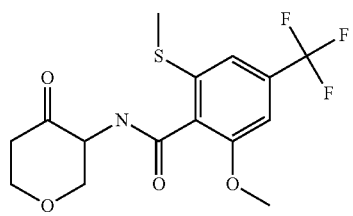 [SMILES: COc1cc(C(F)(F)F)cc(SC)c1C(=O)NC1COCCC1=O]

2-Methoxy-6-methylsulfanyl-4-trifluoromethyl-N-(1,4,8-trioxa-spiro[4.5]dec-6-yl)-benzamide (intermediate B, 200 mg, 0.49 mmol) was dissolved in 1 mL tetrahydrofuran and 1 mL 4N HCl in dioxane was added. The reaction mixture was refluxed for 2 h. The mixture was diluted with water, ethyl acetate and neutralized with saturated sodium bicarbonate solution. The mixture was extracted two times with ethyl acetate. The combined organic layers were dried with sodium sulfate, filtered and evaporated. The crude product was used for the next step.

Intermediate D trans-(4-Bromo-tetrahydro-pyran-3-yl)-carbamic acid tert-butyl ester

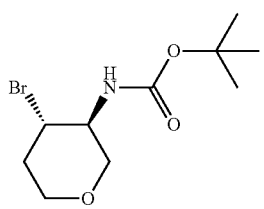

N,N-Dibromo-carbamic acid tert butylester (CAS 358365-86-3) (8.98 g, 28 mmol) was dissolved in 90 mL dichloromethane and cooled to −20° C. Boron trifluoride diethyl etherate (3.99 g, 28 mmol) was added drop-wise and the mixture was stirred at −20° C. for 10 min. A solution of 3,6-dihydro-2H-pyran (2.5 g, 27 mmol) in 20 mL dichloromethane was added drop-wise and stirring was continued at −20° C. for 1 h. The reaction mixture was quenched at +10° C. with 33 mL 12% aqueous sodium sulfite solution. The mixture was extracted three times with dichloromethane. The combined organic phases were dried on sodium sulfate, filtered and evaporated. Purification of the residue by flash chromatography on silica gel (pentane/diethylether 1:0→0:1) yielded the title compound as a white solid (4.24 g, 56%), MS: m/e=223 [(M-buten)⁺].

Intermediate E

3-Oxa-7-aza-bicyclo[4.1.0]heptane-7-carboxylic acid tert-butyl ester

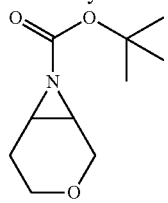

trans-(4-Bromo-tetrahydro-pyran-3-yl)-carbamic acid tert-butyl ester (intermediate D) (1.0 g, 3.5 mmol) was dissolved in 35 mL dimethylformamide. Sodium hydride (60%, 214 mg, 5.4 mmol) was added at 0° O. The reaction mixture was stirred at room temperature for 2 h. The reaction mixture was quenched by careful addition of water. The mixture was extracted three times with diethylether. The combined organic phases were dried on sodium sulfate, filtered and evaporated. Purification of the residue by flash chromatography on silica gel (heptane/ethyl acetate 1:0→1:1) yielded the title compound as a colorless oil (499 mg, 70%), MS: m/e=143 [(M-buten)⁺].

Intermediate F trans-(4-Azido-tetrahydro-pyran-3-yl)-carbamic acid tert-butyl ester

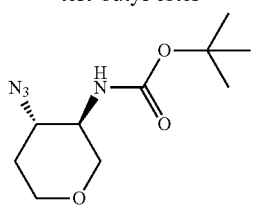

3-Oxa-7-aza-bicyclo[4.1.0]heptane-7-carboxylic acid tert-butyl ester (intermediate E) (5.2 g, 26 mmol) was dissolved in 100 mL acetonitrile. Lithium perchlorate (23 g, 207 mmol) and sodium azide (6.8 g, 104 mmol) were added and the reaction mixture was stirred at 80° C. overnight. 200 mL Water was added. The mixture was extracted three times with diethylether. The combined organic phases were dried on sodium sulfate, filtered and evaporated. Purification of the residue by flash chromatography on silica gel (heptane/ethyl acetate 1:0→1:1) yielded the title compound as a colorless oil (3.3 g, 52%), MS: m/e=186 [(M-butene)⁺].

Intermediate G trans-(4-Amino-tetrahydro-pyran-3-yl)-carbamic acid tert-butyl ester

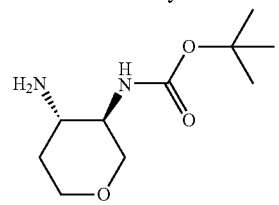

trans-(4-Azido-tetrahydro-pyran-3-yl)-carbamic acid tert-butyl ester (intermediate F) (3.3 g, 14 mmol) was dissolved in 27 mL methanol. Platinum (IV) oxide (307 mg, 1.4 mmol) was added was the reaction mixture was hydrogenated with a H₂-balloon at room temperature overnight. The catalyst was filtered off and the solvent was evaporated off. The crude material, off-white solid (2.74 g, 93%), MS: m/e=161 [(M-buten)⁺] was used without further purification.

Intermediate H trans-(4-Pyrrolidin-1-yl-tetrahydro-pyran-3-yl)-carbamic acid tert-butyl ester

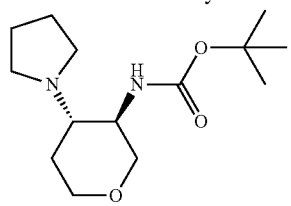

trans-(4-Amino-tetrahydro-pyran-3-yl)-carbamic acid tert-butyl ester (intermediate G, 330 mg, 1.53 mmol) was dissolved in 8 mL acetonitrile. Potassium carbonate (1.05 g, 7.6 mmol) and 1,4-dibromobutane (672 mg, 3.11 mmol) were added and the reaction mixture was refluxed overnight. The solvent was evaporated off. The residue was taken up in water and extracted three times with diethylether. The combined organic phases were dried on sodium sulfate, filtered and evaporated. Purification of the residue by flash chromatography on silica gel (dichloromethane/methanol/ammonia 1:0:0→140:10:1) yielded the title compound as a yellow oil (347 mg, 84%), MS: m/e=271.3 [(M+H)⁺].

Intermediate I trans-(4-Pyrrolidin-1-yl-tetrahydro-pyran-3-ylamine dihydrochloride

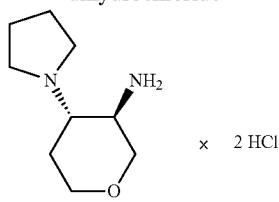

trans-(4-Pyrrolidin-1-yl-tetrahydro-pyran-3-yl)-carbamic acid tert-butyl ester (intermediate H, 345 mg, 1.28 mmol) was dissolved in 6.4 mL dioxane. Hydrochloric acid (4N in dioxan, 3.2 mL, 13 mmol) was added. The reaction mixture was stirred at room temperature for 3 h. The solvent was evaporated off. The crude material, light brown solid (378 mg, >100%), MS: m/e=171.2 [(M+H)$^+$] was used without further purification.

Intermediate J

2-Cyclopropyl-4-trifluoromethyl-benzoic acid

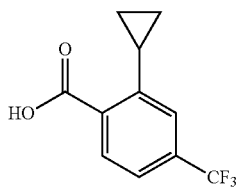

Step 1: 2-Bromo-4-trifluoromethyl-benzoic acid methyl ester

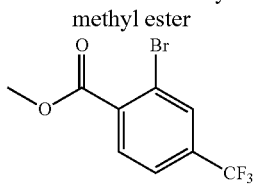

To a solution of 2 g (7.434 mmol) 2-bromo-4-trifluoromethyl-benzoic acid (CAS: 328-89-2) in 20 ml dimethylformamide under nitrogen at room temperature, was added 1.13 g (8.177 mmol) potassium carbonate and 557 ul (8.921 mmol) methyl iodide. The mixture was stirred overnight under nitrogen. The mixture was poured into water (300 ml). The aqueous layer was extracted with ethyl acetate (2×80 ml). The combined extracts were dried over sodium sulfate, filtered and concentrated in vacuo. The crude oil was purified on silica gel (eluent: heptane/ethyl acetate 0 to 10%) to provide 1.75 g (83%) of the title compound as an orange oil.

Step 2: 2-Cyclopropyl-4-trifluoromethyl-benzoic acid methyl ester

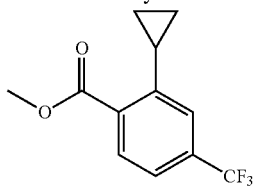

To a solution of 400 mg (1.413 mmol) 2-bromo-4-trifluoromethyl-benzoic acid methyl ester, 146 mg (1.696 mmol) cyclopropyl boronic acid, 1.21 g (4.946 mmol) tri-potassium phosphate monohydrate and 40.9 mg (0.141 mmol) tricyclohexyl phosphine in 6 ml toluene and 0.3 ml water under nitrogen at room temperature, was added 15.9 mg (0.0707 mmol) palladium acetate. The mixture was stirred in a 100° C. oil bath for 4 hours and overnight at room temperature under nitrogen. The mixture was cooled to room temperature. Water was added and the mixture extracted with ethyl acetate. The organic layer was washed once with brine, dried over sodium sulfate, filtered and concentrated in vacuo. The crude compound was purified on silica gel (eluent: heptane/ethyl acetate 0 to 10%) to provide 0.24 g (71%) of the title compound as a yellow oil.

Step 3: 2-Cyclopropyl-4-trifluoromethyl-benzoic acid

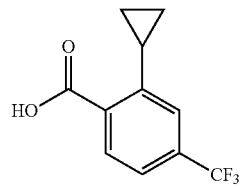 [SMILES: O=C(O)c1ccc(C(F)(F)F)cc1C1CC1]

To a suspension of 485 mg (1.986 mmol) 2-cyclopropyl-4-trifluoromethyl-benzoic acid methyl ester in 8 ml ethanol at room temperature, was added 1.99 ml (3.972 mmol) 2N NaOH. The mixture was heated in an 80° C. oil bath for 30 minutes. The solution was cooled to room temperature and the ethanol was evaporated. The residue was diluted with water, acidified with 2N HCl to pH 2 and dichloromethane was added. The aqueous phase was extracted twice with dichloromethane. The combined organic phases were dried over sodium sulfate, filtered and concentrated in vacuo. The crude product was purified on silica gel (eluent: heptane/ethyl acetate 0 to 100%) to provide 0.197 g (27%) of the title compound as a light yellow solid. MS (m/e): 229.0 (M−H).

Intermediate K trans-(4-Cyclopentylamino-tetrahydro-pyran-3-yl)-carbamic acid tert-butyl ester

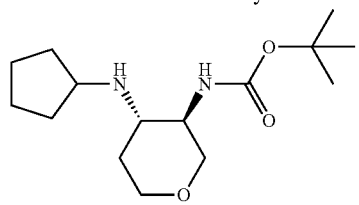

trans-(4-Amino-tetrahydro-pyran-3-yl)-carbamic acid tert-butyl ester (intermediate G, 1.0 g, 4.63 mmol) was dissolved in 90 mL methanol. Acetic acid (1.4 g, 23 mmol) and cyclopentanone (1.18 g, 14 mmol) were added and the reaction mixture was stirred at 45° C. overnight. Sodium cyanoborohydride (612 mg, 9.7 mmol) was added and stirring was continued at 45° C. for 2 h. The mixture was extracted with 2N sodium carbonate solution and ethyl acetate. The combined organic phases were dried on sodium sulfate, filtered and evaporated. Purification of the residue by flash chromatography on silica gel (dichloromethane/methanol/ammonia 100:0:0→90:10:1) yielded the title compound as a yellow solid (815 mg, 62%), MS: m/e=229.4 [(M-butene)$^+$].

Intermediate L trans-N-4-Cyclopentyl-tetrahydro-pyran-3,4-diamine dihydrochloride

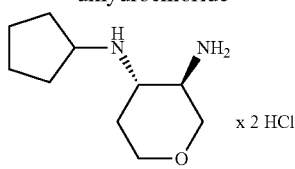

The title compound, light brown solid, MS: m/e=185.2 [(M+H)$^+$], was prepared in accordance with the general method of intermediate I from trans-(4-cyclopentylamino-tetrahydro-pyran-3-yl)-carbamic acid tert-butyl ester (intermediate K).

Intermediate M

Butyl-[1-(2-fluoro-4,6-bis-trifluoromethyl-phenyl)-methylidene]-amine

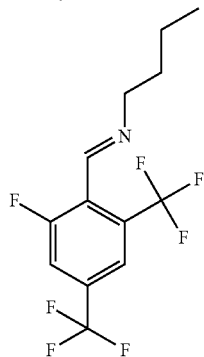 [SMILES: CCCC/N=C/c1c(F)cc(C(F)(F)F)cc1C(F)(F)F]

2-Fluoro-4,6-bis(trifluoromethyl)benzaldehyde (10 g, 38 mmol) was dissolved in 30 mL toluene. p-Toluenesulfonic acid (140 mg, 0.74 mmol) and N-butylamine (2.94 g, 40 mmol) were added. The reaction mixture was refluxed overnight. The mixture was extracted with 2N sodium carbonate solution and ethyl acetate. The combined organic phases were dried on sodium sulfate, filtered and evaporated. The crude material, orange oil (12 g, >100%) was used without further purification.

Intermediate N

Butyl-[1-(2-cyclopropyl-4,6-bis-trifluoromethyl-phenyl)-methylidene]-amine

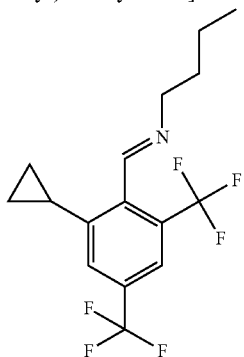

Cyclopropylbromide (3.84 g, 32 mmol) was added to magnesium (771 mg, 32 mmol) in 20 mL diethylether and refluxed for 10 min. Manganese(II) chloride (160 mg, 1.27 mmol) and butyl-[1-(2-fluoro-4,6-bis-trifluoromethyl-phenyl)-methylidene]-amine (intermediate M, 4 g, 13 mmol) was added. The reaction mixture was refluxed for 2 h. The reaction mixture was quenched with 8 mL water and filtered through dicalite. The organic phase was separated and dried on sodium sulfate, filtered and evaporated. The crude material, brown oil (3.54 g, 82%) was used without further purification.

Intermediate O

2-Cyclopropyl-4,6-bis-trifluoromethyl-benzaldehyde

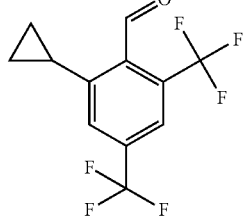

Crude butyl-[1-(2-cyclopropyl-4,6-bis-trifluoromethyl-phenyl)-methylidene]-amine (intermediate M, 3.54 g, 10.5 mmol) was dissolved in 8 mL water. Hydrochloric acid (25%, 0.49 mL) was added and the mixture was refluxed for 2 h. The mixture was extracted three times with ethyl acetate. The combined organic phases were dried on sodium sulfate, filtered and evaporated. The crude material, brown oil (1.01 g, 34%) was used without further purification.

Intermediate P

2-Cyclopropyl-4,6-bis-trifluoromethyl-benzoic acid

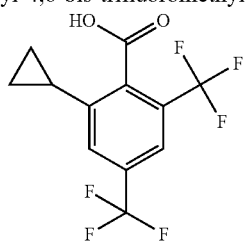

Crude 2-cyclopropyl-4,6-bis-trifluoromethyl-benzaldehyde (intermediate O, 1.01 g, 3.58 mmol) was dissolved in 8.5 mL tert-butylalcohol and 4.5 mL 2-methyl-2-butene. At 0° C. a solution of sodium chlorite (340 mg, 3.76 mmol) and sodium dihydrogenphosphat (451 mg, 3.76 mmol) in 3 mL water was added. The reaction mixture was stirred at room temperature overnight. The solvents were evaporated off. The residue was taken up in 1N NaOH and extracted twice with tert-butyl methyl ether. The aqueous phase was adjusted to pH 2 by addition of 25% HCl and extracted twice with tert-butyl methyl ether. The combined organic phases were dried on sodium sulfate, filtered and evaporated. The crude material, off-white solid (1.01 g, 54%) was used without further purification.

Intermediate Q trans-N,4-cyclohexyl-tetrahydro-pyran-3,4-diamine hydrochloride

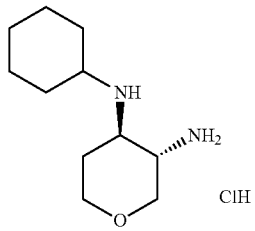 [SMILES: N[C@@H]1COCC[C@H]1NC1CCCCC1 ; Cl]

The title compound, white solid, MS: m/e=199.4 [(M+H)+], was prepared in accordance with the general method of intermediate L from trans-4-cyclohexylamino-tetrahydro-pyran-3-yl)-carbamic acid tert-butyl ester which itself was prepared following procedure described for intermediate K from trans-(4-amino-tetrahydro-pyran-3-yl)-carbamic acid tert-butyl ester (intermediate G) and cyclopentanone.

Intermediate R trans-N-4-Isopropyl-tetrahydro-pyran-3,4-diamine hydrochloride

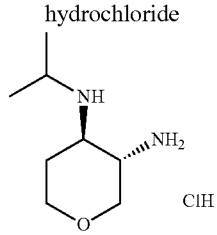

The title compound, white solid, MS: m/e=159.3 [(M+H)+], was prepared in accordance with the general method of intermediate L from trans-4-isopropylamino-tetrahydro-pyran-3-yl)-carbamic acid tert-butyl ester which itself was prepared following procedure described for intermediate K from trans-(4-amino-tetrahydro-pyran-3-yl)-carbamic acid tert-butyl ester (intermediate G) and acetone.

Intermediate S trans-N-4-(Tetrahydro-pyran-4-yl)-tetrahydro-pyran-3,4-diamine dihydrochloride

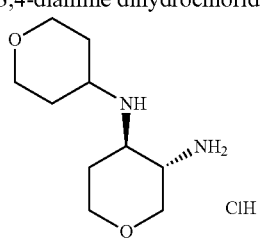

The title compound, white solid, MS: m/e=201.3 [(M+H)+], was prepared in accordance with the general method of intermediate L from trans-[4-(tetrahydro-pyran-4-ylamino)-tetrahydro-pyran-3-yl]-carbamic acid tert-butyl ester which itself was prepared following procedure described for intermediate K from trans-(4-amino-tetrahydro-pyran-3-yl)-carbamic acid tert-butyl ester (intermediate G) and tetrahydropyranone.

Intermediate T trans-N-4-Cyclopropylmethyl-tetrahydro-pyran-3,4-diamine dihydrochloride

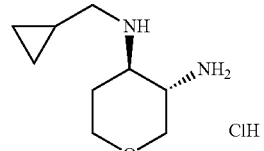

The title compound, white solid, MS: m/e=171.3 [(M+H)+], was prepared in accordance with the general method of intermediate L from trans-4-(cyclopropylmethyl-amino)-tetrahydro-pyran-3-yl]-carbamic acid tert-butyl ester which itself was prepared following procedure described for intermediate K from trans-(4-amino-tetrahydro-pyran-3-yl)-carbamic acid tert-butyl ester (intermediate G) and cyclopropanecarbaldehyde.

Intermediate U trans-4-Piperidin-1-yl-tetrahydro-pyran-3-yl-amine dihydrochloride

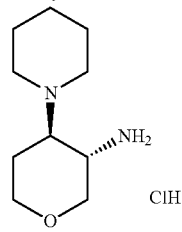

The title compound, white solid, MS: m/e=185.2 [(M+H)+], was prepared in accordance with the general method of intermediate L from trans-4-piperidin-1-yl-tetrahydro-pyran-3-yl)-carbamic acid tert-butyl ester which itself was prepared following procedure described for intermediate H from trans-(4-amino-tetrahydro-pyran-3-yl)-carbamic acid tert-butyl ester (intermediate G) and 1,5-dibromopropane.

Intermediate V trans-N-4-Cyclopropyl-tetrahydro-pyran-3,4-diamine dihydrochloride

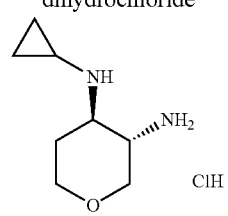

The title compound, white solid, MS: m/e=157.3 [(M+H)+], was prepared in accordance with the general method of intermediate L from trans-4-cyclopropylamino-tetrahydro-pyran-3-yl)-carbamic acid tert-butyl ester which itself was prepared following procedure described for intermediate K from trans-(4-amino-tetrahydro-pyran-3-yl)-carbamic acid tert-butyl ester (intermediate G) and [(1-ethoxycyclopropyl)oxy]-trimethylsilane

Intermediate W trans-4-(1-Methyl-cyclohexylamino)-tetrahydro-pyran-3-yl]-carbamic acid tert-butyl ester

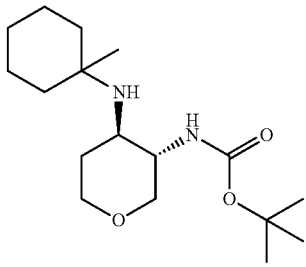 [SMILES: CC1(N[C@@H]2CCOC[C@H]2NC(=O)OC(C)(C)C)CCCCC1]

To a solution of 350 mg (1.405 mmol) 3-oxa-7-aza-bicyclo[4.1.0]heptane-7-carboxylic acid tert-butyl ester (intermediate E) in 6.0 ml acetonitrile were added 430 mg (2.8 mmol) 1-amino-1-methylcyclohexane hydrochloride (CAS: 89854-70-6), 505 ul (2.951 mmol) N-ethyldiisopropylamine and 1.2 g (11.24 mmol) lithium perchlorate. The mixture was heated at 70° C. for 6 hours and then stirred at room temperature overnight. The mixture was cooled to room temperature and diluted with dichloromethane. The solution was washed once with water. The washings were extracted once with dichloromethane. The combined organic phases were dried over sodium sulfate, filtered and concentrated in vacuo. Purification of the residue by flash chromatography on silica gel (heptane, ethylacetate 100:0→0:100) yielded the title compound as a light yellow solid (53 mg, 12%), MS: m/e=313.2 [M+H$^+$].

Intermediate X trans-N-4-(1-Methyl-cyclohexyl)-tetrahydro-pyran-3,4-diamine dihydrochloride

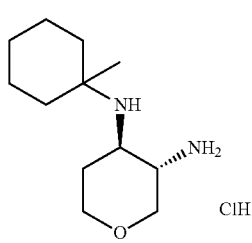

The title compound, white solid, MS: m/e=213.4 [(M+H)$^+$], was prepared in accordance with the general method of intermediate L from trans-4-(1-Methyl-cyclohexylamino)-tetrahydro-pyran-3-yl]-carbamic acid tert-butyl ester.

Intermediate Y trans-N-4-(1-Methyl-cyclopentyl)-tetrahydro-pyran-3,4-diamine hydrochloride

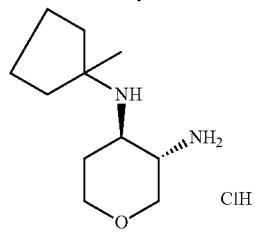

The title compound, white solid, MS: m/e=199.3 [(M+H)$^+$], was prepared in accordance with the general method of intermediate L from trans-4-(1-Methyl-cyclopentylamino)-tetrahydro-pyran-3-yl]-carbamic acid-tert-butyl ester which itself was prepared following procedure described for intermediate W from 3-oxa-7-aza-bicyclo[4.1.0]heptane-7-carboxylic acid tert-butyl ester (intermediate E) and 1-amino-1-methylcyclopentane hydrochloride (CAS: 102014-58-4).

Intermediate Z trans-N-4-(1-Cyclopropyl-ethyl)-tetrahydro-pyran-3,4-diamine dihydrochloride

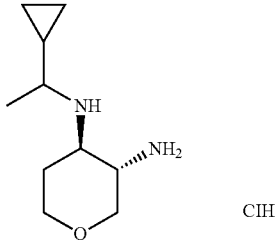

The title compound, white solid, MS: m/e=185.2 [(M+H)$^+$], was prepared in accordance with the general method of intermediate L from trans-4-(1-cyclopropyl-ethylamino)-tetrahydro-pyran-3-yl]-carbamic acid tert-butyl ester which itself was prepared following procedure described for intermediate K from trans-(4-amino-tetrahydro-pyran-3-yl)-carbamic acid tert-butyl ester (intermediate G) and 1-cyclopropyl-ethanone.

Intermediate AA trans-N-4-Cyclobutyl-tetrahydro-pyran-3,4-diamine dihydrochloride

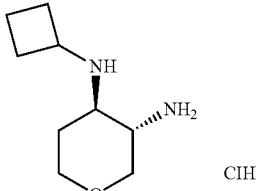

The title compound, white solid, MS: m/e=171.3 [(M+H)$^+$], was prepared in accordance with the general method of intermediate L from trans-4-cyclobutylamino-tetrahydro-pyran-3-yl)-carbamic acid tert-butyl ester which itself was prepared following procedure described for intermediate K from trans-(4-amino-tetrahydro-pyran-3-yl)-carbamic acid tert-butyl ester (intermediate G) and cyclobutanone.

Intermediate AB trans-4-3-Amino-tetrahydro-pyran-4-ylamino)-cyclohexanol dihydrochloride

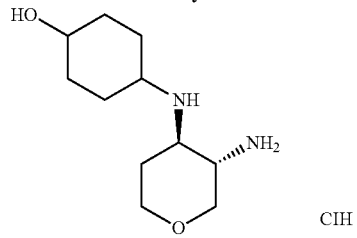

The title compound, white solid, MS: m/e=215.4 [(M+H)⁺], was prepared in accordance with the general method of intermediate L from trans-4-(4-hydroxy-cyclohexylamino)-tetrahydro-pyran-3-yl]-carbamic acid tert-butyl ester which itself was prepared following procedure described for intermediate K from trans-(4-amino-tetrahydro-pyran-3-yl)-carbamic acid tert-butyl ester (intermediate G) and 4-hydroxy-cyclohexanone.

Intermediate AC trans-4-(3-Aza-bicyclo[3.1.0]hex-3-yl)-tetrahydro-pyran-3-ylamine dihydrochloride

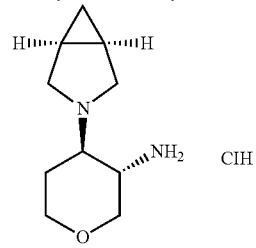

The title compound, white solid, MS: m/e=183.2 [(M+H)⁺], was prepared in accordance with the general method of intermediate L from trans-4-(3-aza-bicyclo[3.1.0]hex-3-yl)-tetrahydro-pyran-3-yl]-carbamic acid tert-butyl ester which itself was prepared following procedure described for intermediate W from 3-oxa-7-aza-bicyclo[4.1.0]heptane-7-carboxylic acid tert-butyl ester (intermediate E) and 3-Aza-bicyclo[3.1.0]hexane hydrochloride (CAS: 73799-64-1).

Intermediate AD 2,6-Dimethyl-4-trifluoromethyl-benzoic acid

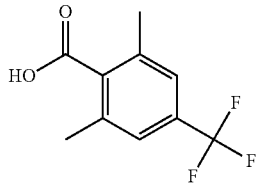

Step 1. Preparation of 2,6-Dimethoxy-4-trifluoromethyl-benzoic acid

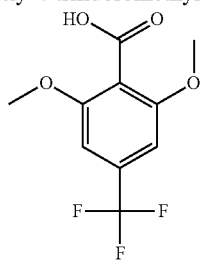

To a solution of sodium hydroxide (5.66 g, 141.4 mmol) in 33 ml water and 33 ml ethanol at room temperature under nitrogen, was added 2,6-dimethoxy-4-trifluoromethyl-benzonitrile (CAS: 51271-36-4) (3.27 g, 14.14 mmol). The reaction mixture was heated in a 90° C. oil bath for 37 hours. The reaction mixture was cooled to room temperature and 130 ml water was added. The product was collected by filtration and dried to provide 3.05 g of an off-white solid. To a solution of nitrosylsulfuric acid (15.6 g, 110.2 mmol) in 9.5 ml water at 0° C. under nitrogen, was added drop-wise a suspension of the previously obtained material in 19 ml dichloromethane. The reaction mixture was stirred at 0° C. for 4.5 h. The reaction mixture was poured over ice and extracted with dichloromethane. The combined organic layers were dried over $Na_2SO_4$, filtered and dried to provide 1.51 g of product. The aqueous phase was filtered and the white solid was dried to provide 1.36 g of product. Both batches were mixed to provide 2.87 g (93.7%) of the title compound as a white solid. MS (m/e): 249.1 (M–H).

Step 2. Preparation of 2,6-Dimethoxy-4-trifluoromethyl-benzoyl chloride

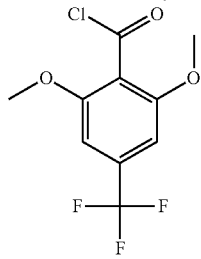

To a suspension of 14.47 g (57.84 mmol) 2,6-dimethoxy-4-trifluoromethyl-benzoic acid in 160 ml toluene containing four drops DMF under nitrogen at room temperature, was added 42 ml (578.4 mmol) thionyl chloride. The mixture was heated in an 85° C. oil bath for 3 hours. The solvent was removed in vacuo to provide 15.37 g (yield: 98.9%) of the title compound as an off-white solid.

Step 3. Preparation of N-(2-Hydroxy-1,1-dimethyl-ethyl)-2,6-dimethoxy-4-trifluoromethyl-benzamide

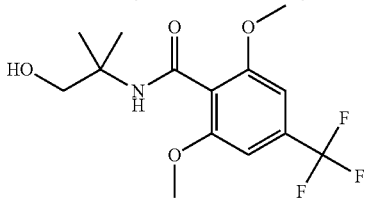 [SMILES: COc1cc(C(F)(F)F)cc(OC)c1C(=O)NC(C)(C)CO]

To a solution of 3.7 ml (37.22 mmol) 2-amino-2-methyl-1-propanol in 42 ml dichloromethane under nitrogen at 0° C., was added dropwise a solution of 5 g (18.61 mmol) 2,6-dimethoxy-4-trifluoromethyl-benzoyl chloride in 12 ml dichloromethane. The temperature rose to 7° C. The mixture was stirred at room temperature for 4 hours. The mixture was poured onto 75 ml water. The organic layer was separated and the aqueous layer was extracted twice with dichloromethane. The combined organic layers were washed with brine, dried over sodium sulfate, filtered and concentrated in vacuo to provide 5.66 g (yield: 94.6%) of the title compound as a yellow solid. MS (m/e): 322.2 (M+H$^+$).

Step 4. Preparation of 2-(2,6-Dimethoxy-4-trifluoromethyl-phenyl)-4,4-dimethyl-4,5-dihydro-oxazole

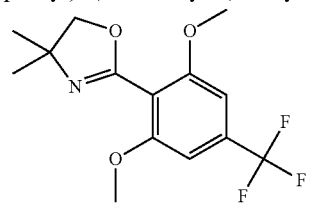

A solution of 5.66 g (17.62 mmol) N-(2-hydroxy-1,1-dimethyl-ethyl)-2,6-dimethoxy-4-trifluoromethyl-benzamide in 60 ml dichloromethane was cooled to 10° C. 3.8 ml (52.85 mmol) thionylchloride was added drop-wise. The temperature rose to 15° C. The mixture was stirred at room temperature for 1 hour. The solution was added drop-wise to 130 ml of a cooled 2M sodium carbonate solution. The emulsion was diluted with water and filtered, to remove the white solid. The organic layer was separated and the aqueous layer was extracted twice with dichloromethane. The combined extracts were dried over sodium sulfate, filtered and concentrated in vacuo. The crude light yellow solid (5.27 g) was purified with flash column chromatography on silica (70 g) eluting with a gradient formed from n-heptane and ethyl acetate (0 to 50%) to provide 4.8 g (yield: 89.8%) of the title compound as a white solid. MS (m/e): 304.2 (M+H$^+$).

Step 5. Preparation of 2-(2,6-Dimethyl-4-trifluoromethyl-phenyl)-4,4-dimethyl-4,5-dihydro-oxazole (compound A)

and 2-(2-Methoxy-6-methyl-4-trifluoromethyl-phenyl)-4,4-dimethyl-4,5-dihydro-oxazole (compound B)

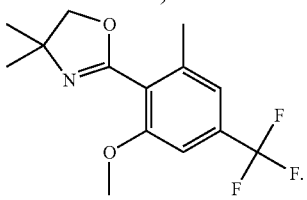

To a 0° C. solution of 1.5 g (4.946 mmol) 2-(2,6-dimethoxy-4-trifluoromethyl-phenyl)-4,4-dimethyl-4,5-dihydro-oxazole in 9 ml tetrahydrofuran over mol-sieve, was added dropwise 9.89 ml (29.68 mmol) of a 3M methylmagnesium bromide solution in diethyl ether maintaining the temperature below 5° C. The mixture was allowed to warm to room temperature and was then heated in a 70° C. oil bath for 24 hours. The mixture was cooled in an ice bath and quenched with 60 ml of a saturated ammonium solution. Ethyl acetate was added. The organic layer was separated and the aqueous layer was extracted once with ethyl acetate. The combined extracts were dried over sodium sulfate, filtered and concentrated in vacuo. The crude orange oil (1.38 g) was purified with flash column chromatography on silica eluting with a gradient formed from n-heptane and ethyl acetate (0 to 35%) to provide 419 mg (yield: 31.2%) of 2-(2,6-dimethyl-4-trifluoromethyl-phenyl)-4,4-dimethyl-4,5-dihydro-oxazole (compound A) as a white solid. MS (m/e): 272.2 (M+H$^+$) and 532 mg (yield: 37.4%) of 2-(2-Methoxy-6-methyl-4-trifluoromethyl-phenyl)-4,4-dimethyl-4,5-dihydro-oxazole (compound B) as a colorless oil. MS (m/e): 288.1 (M+H$^+$)

Step 6. Preparation of 2,6-Dimethyl-4-trifluoromethyl-benzoic acid 2-methyl-2-nitro-propyl ester

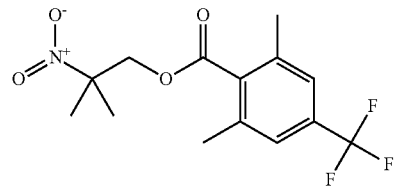 [SMILES: Cc1cc(C(F)(F)F)cc(C)c1C(=O)OCC(C)(C)[N+](=O)[O-]]

To a solution of 415 mg (1.530 mmol) 2-(2,6-dimethyl-4-trifluoromethyl-phenyl)-4,4-dimethyl-4,5-dihydro-oxazole in 17 ml acetonitrile was added 15.3 ml (0.0061 mmol) of an 0.4 mM aqueous Na$_2$-EDTA solution at room temperature. 1.4 ml (15.30 mmol) 1,1,1-trifluoroacetone was added at once with a pre-cooled syringe. A mixture of 3.86 g (45.90 mmol) sodiumbicarbonate and 9.41 g (15.30 mmol) oxone was added portion-wise over a period of 15 minutes. The mixture was stirred for 30 minutes. The reaction mixture was diluted with 90 ml water. The aqueous layer was extracted 3 times with dichloromethane. The combined extracts were dried over sodium sulfate, filtered and concentrated in vacuo to provide 477 mg (y: 97.7%) of the title compound as a colorless oil.

Step 7. Preparation of 2,6-Dimethyl-4-trifluoromethyl-benzoic acid

To a solution of 475 mg (1.488 mmol) 2,6-dimethyl-4-trifluoromethyl-benzoic acid 2-methyl-2-nitro-propyl ester in 4.7 ml dioxane was added 3 ml (14.88 mmol) of a 5M aqueous NaOH solution. The mixture was heated in a 100° C. oil bath for 24 hours. The dioxane was removed in vacuo. The residue was diluted with water and extracted twice with ethyl acetate. The aqueous layer was acidified with HCl 5N and extracted 3 times with dichloromethane. The combined dichloromethane extracts were dried over sodium sulfate, filtered and concentrated in vacuo to provide 301 mg (y: 92.7%) of the title compound as a light yellow solid. MS (m/e): 217.1 (M–H).

Intermediate AE

2-Methoxy-6-methyl-4-trifluoromethyl-benzoic acid

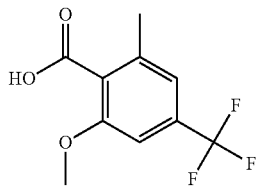 [SMILES: COc1cc(C(F)(F)F)cc(C)c1C(=O)O]

The title compound, light yellow solid, MS: m/e=232.9 (M–H), was prepared according to the procedure described for intermediate AD from 2-(2-methoxy-6-methyl-4-trifluoromethyl-phenyl)-4,4-dimethyl-4,5-dihydro-oxazole (intermediate AD, step 5, compound B).

Intermediate AF 2,6-Diethyl-4-trifluoromethyl-benzoic acid

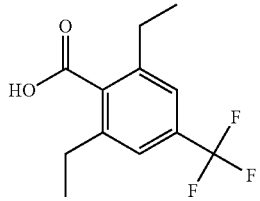 [SMILES: CCc1cc(C(F)(F)F)cc(CC)c1C(=O)O]

The title compound, light yellow solid, MS: m/e=245.1 (M–H), was prepared according to the procedure described for intermediate AD from 2-(2,6-dimethoxy-4-trifluoromethyl-phenyl)-4,4-dimethyl-4,5-dihydro-oxazole using ethylmagnesium bromide as a Grignard reagent.

Intermediate AG

2-Ethyl-6-methoxy-4-trifluoromethyl-benzoic acid

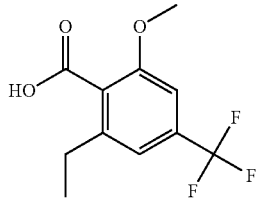 [SMILES: CCc1cc(C(F)(F)F)cc(OC)c1C(=O)O]

The title compound, light yellow solid, MS: m/e=247.0 (M–H), was prepared according to the procedure described for intermediate AD from 2-(2,6-dimethoxy-4-trifluoromethyl-phenyl)-4,4-dimethyl-4,5-dihydro-oxazole using ethylmagnesium bromide as a Grignard reagent.

Intermediate AH

2-Ethyl-6-methyl-4-trifluoromethyl-benzoic acid

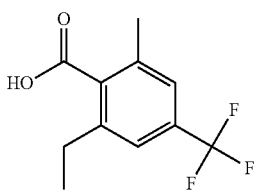 [SMILES: CCc1cc(C(F)(F)F)cc(C)c1C(=O)O]

Step 1: 2-(2-Ethyl-6-methyl-4-trifluoromethyl-phenyl)-4,4-dimethyl-4,5-dihydro-oxazole

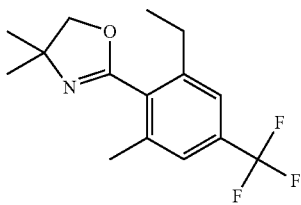 [SMILES: CCc1cc(C(F)(F)F)cc(C)c1C1=NC(C)(C)CO1]

To a 0° C. solution of 100 mg (0.332 mmol) 2-(2-ethyl-6-methoxy-4-trifluoromethyl-phenyl)-4,4-dimethyl-4,5-dihydro-oxazole (obtained by reaction of 2-(2,6-dimethoxy-4-trifluoromethyl-phenyl)-4,4-dimethyl-4,5-dihydro-oxazole with ethylmagnesium bromide) in 0.6 ml tetrahydrofuran, was added drop-wise 0.332 ml (0.996 mmol) of a 3M methylmagnesium bromide solution in diethyl ether maintaining the temperature below 5° C. The mixture was allowed to warm to room temperature and stirred for 3.5 hours and then heated in a 70° C. oil bath for 4 days. The mixture was cooled in an ice bath and quenched dropwise with 3 ml saturated ammonium chloride solution. Ethyl acetate was added. The organic layer was separated and the aqueous layer was extracted three times with ethyl acetate. The combined extracts were dried over sodium sulfate, filtered and concentrated in vacuo. The crude orange oil (286 mg) was purified with flash column chromatography on silica eluting with a gradient formed from n-heptane and ethyl acetate (0 to 10%) to provide 50 mg (yield: 50.4%) of the title compound as a light yellow oil. MS (m/e): 286.2 (M+H$^+$).

Step 2: 2-Ethyl-6-methyl-4-trifluoromethyl-benzoic acid

The title compound, light yellow solid, MS: m/e=245.1 (M–H), was prepared according to the procedure described for intermediate AD (step 6-7) from 2-(2-Ethyl-6-methyl-4-trifluoromethyl-phenyl)-4,4-dimethyl-4,5-dihydro-oxazole.

Intermediate AI

2-Cyclopropyl-6-methoxy-4-trifluoromethyl-benzoic acid

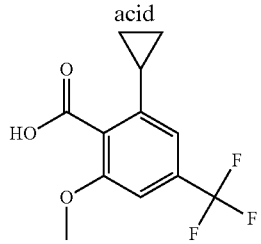

The title compound, off-white solid, MS: m/e=258.9 (M−H), was prepared according to the procedure described for intermediate AD from 2-(2,6-dimethoxy-4-trifluoromethyl-phenyl)-4,4-dimethyl-4,5-dihydro-oxazole using cyclopropylmagnesium bromide as a Grignard reagent.

Intermediate AJ trans-4-(2-Aza-bicyclo[3.1.0]hex-2-yl)-tetrahydro-pyran-3-ylamine hydrochloride-diastereoisomer 1

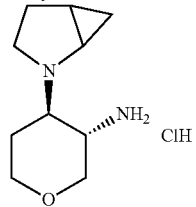

The title compound, yellow solid, MS: m/e=183.2 [(M+H)$^+$], was prepared in accordance with the general method of intermediate L from trans-4-(2-aza-bicyclo[3.1.0]hex-2-yl)-tetrahydro-pyran-3-yl]-carbamic acid tert-butyl ester (diastereoisomer 1) which itself was prepared following procedure described for intermediate W from 3-oxa-7-aza-bicyclo[4.1.0]heptane-7-carboxylic acid tert-butyl ester (intermediate E) and 2-aza-bicyclo[3.1.0]hexane hydrochloride (CAS: 841302-37-2).

Intermediate AK trans-4-(2-Aza-bicyclo[3.1.0]hex-2-yl)-tetrahydro-pyran-3-ylamine hydrochloride-diastereoisomer 2

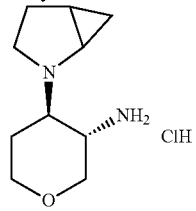

The title compound, yellow solid, MS: m/e=183.2 [(M+H)$^+$], was prepared in accordance with the general method of intermediate L from trans-4-(2-aza-bicyclo[3.1.0]hex-2-yl)-tetrahydro-pyran-3-yl]-carbamic acid tert-butyl ester (diastereoisomer 2) which itself was prepared following procedure described for intermediate W from 3-oxa-7-aza-bicyclo[4.1.0]heptane-7-carboxylic acid tert-butyl ester (intermediate E) and 2-aza-bicyclo[3.1.0]hexane hydrochloride (CAS: 841302-37-2).

Intermediate AL trans-1-(3-Amino-tetrahydro-pyran-4-yl)-pyrrolidin-3-ol dihydrochlorid-diastereoisomer 1

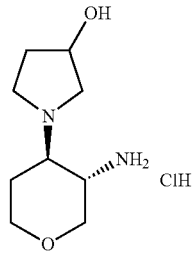 [SMILES: N[C@@H]1COCC[C@H]1N1CCC(O)C1 ; Cl]

The title compound, light brown solid, MS: m/e=187.3 [(M+H)$^+$], was prepared in accordance with the general method of intermediate L from trans-4-(3-hydroxy-pyrrolidin-1-yl)-tetrahydro-pyran-3-yl]-carbamic acid tert-butyl ester diastereoisomer 1 which itself was prepared following the procedure described for intermediate H from trans-(4-amino-tetrahydro-pyran-3-yl)-carbamic acid tert-butyl ester (intermediate G) and 1,4-dibromo-2-butanol.

Intermediate AM trans-1-(3-Amino-tetrahydro-pyran-4-yl)-pyrrolidin-3-ol dihydrochlorid-diastereoisomer 2

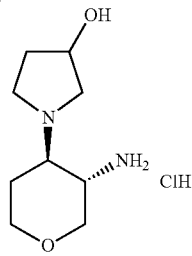 [SMILES: N[C@@H]1COCC[C@H]1N1CCC(O)C1 ; Cl]

The title compound, light brown solid, MS: m/e=187.3 [(M+H)$^+$], was prepared in accordance with the general method of intermediate L from trans-4-(3-hydroxy-pyrrolidin-1-yl)-tetrahydro-pyran-3-yl]-carbamic acid tert-butyl ester diastereoisomer 2 which itself was prepared following procedure described for intermediate H from trans-(4-amino-tetrahydro-pyran-3-yl)-carbamic acid tert-butyl ester (intermediate G) and 1,4-dibromo-2-butanol.

Intermediate AN (4-Amino-tetrahydro-pyran-3-yl)-carbamic acid tert-butyl ester (mixture of diastereomers)

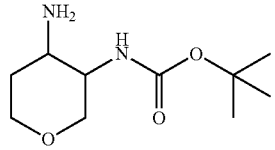

(4-Oxo-tetrahydro-pyran-3-yl)-carbamic acid tert-butyl ester (CAS 477584-38-6, 446 mg, 2.07 mmol) was dissolved in 20 mL methanol. Ammonium acetate (1.63 g, 21 mmol) and sodium cyanoborohydride (507 mg, 8.1 mmol) were added and the reaction mixture was stirred at room temperature for 2 days. Ethyl acetate and 2N sodium carbonate solution were added. The organic layer was separated and the aqueous layer was extracted three times with ethyl acetate. The combined extracts were dried over sodium sulfate, filtered and concentrated in vacuo. The residue was purified with flash column chromatography on silica eluting with a gradient (dichloromethane/methanol/ammonia 100:0:0→140:10:1) to provide 199 mg (44%) of the title compound as a white solid. MS (m/e): 161.2 (M-butene)⁺.

Intermediate AO

[4-(2-Methoxy-6-methylsulfanyl-4-trifluoromethyl-benzoylamino)-tetrahydro-pyran-3-yl]-carbamic acid tert-butyl ester (mixture of diastereomers)

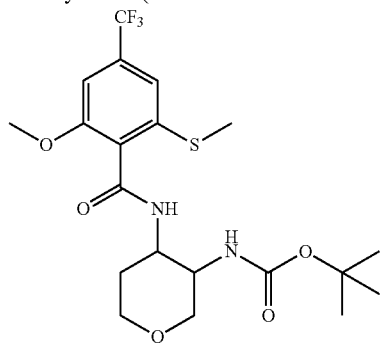

The title compound, white solid, MS: m/e=465.3 [(M+H)⁺], was prepared in accordance with the general method of example 8 from (4-amino-tetrahydro-pyran-3-yl)-carbamic acid tert-butyl ester (mixture of diastereomers, intermediate AM) and 2-methoxy-6-methylsulfanyl-4-trifluoromethyl-benzoic acid (intermediate A).

Intermediate AP

N-(3-Amino-tetrahydro-pyran-4-yl)-2-methoxy-6-methylsulfanyl-4-trifluoromethyl-benzamide hydrochloride (mixture of diastereomers)

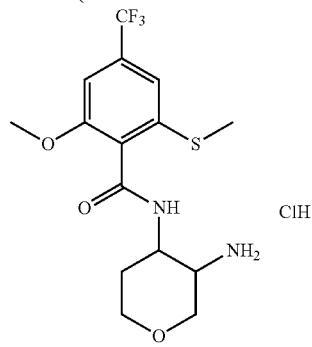

The title compound, white solid, MS: m/e=365.1 [(M+H)⁺], was prepared in accordance with the general method of intermediate I from [4-(2-methoxy-6-methylsulfanyl-4-trifluoromethyl-benzoylamino)-tetrahydro-pyran-3-yl]-carbamic acid tert-butyl ester (mixture of diastereomers, intermediate AO).

SYNTHESIS OF THE EXAMPLES

Examples 1 and 2

2-Methoxy-6-methylsulfanyl-N-((3RS,4RS)-4-pyrrolidin-1-yl-tetrahydro-pyran-3-yl)-4-trifluoromethyl-benzamide and 2-Methoxy-6-methylsulfanyl-N-((3RS,4SR)-4-pyrrolidin-1-yl-tetrahydro-pyran-3-yl)-4-trifluoromethyl-benzamide

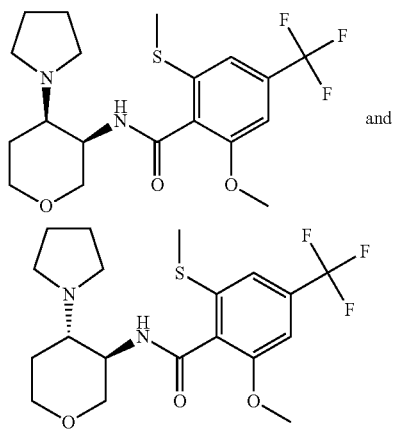

2-Methoxy-6-methylsulfanyl-N-(4-oxo-tetrahydro-pyran-3-yl)-4-trifluoromethyl-benzamide (intermediate C, 300 mg, 0.83 mmol) was dissolved in 5 mL tetrahydrofurane. Acetic acid (86 mg, 1.4 mmol) and pyrrolidine (70 mg, 0.99 mmol) were added and the reaction mixture was stirred 1 h at room temperature. Sodium triacetoxyborohydride (209 mg, 0.99 mmol) was added and stirring was continued at room temperature overnight. The mixture was extracted with 2N sodium carbonate solution and ethyl acetate. The combined organic phases were dried on sodium sulfate, filtered and evaporated. Purification of the residue by flash chromatography on silica gel (dichloromethane/methanol/ammonia 100:0:0→140:10:1) yielded cis-2-methoxy-6-methylsulfanyl-N-((3RS,4RS)-4-pyrrolidin-1-yl-tetrahydro-pyran-3-yl)-4-trifluoromethyl-benzamide as a light brown solid (80 mg, 40%), MS: m/e=419.1 [(M+H)] and trans-2-methoxy-6-methylsulfanyl-N-((3RS,4SR)-4-pyrrolidin-1-yl-tetrahydro-pyran-3-yl)-4-trifluoromethyl-benzamide as a light brown solid (25 mg, 12%), MS: m/e=419.1 [(M+H)⁺].

Examples 3 and 4

N-((3RS,4RS)-4-Cyclobutylamino-tetrahydro-pyran-3-yl)-2-methoxy-6-methylsulfanyl-4-trifluoromethyl-benzamide and N-((3RS,4SR)-4-Cyclobutylamino-tetrahydro-pyran-3-yl)-2-methoxy-6-methylsulfanyl-4-trifluoromethyl-benzamide

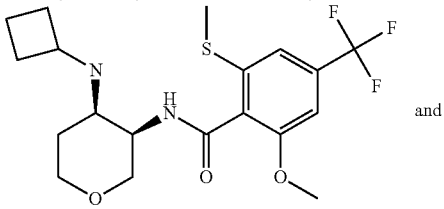

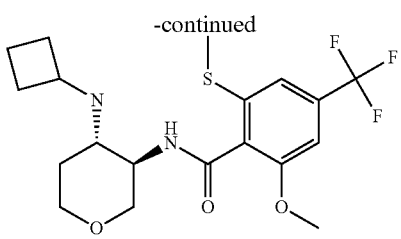

cis-N-((3RS,4RS)-4-Cyclobutylamino-tetrahydro-pyran-3-yl)-2-methoxy-6-methylsulfanyl-4-trifluoromethyl-benzamide, light brown solid, MS: m/e=419.2 [(M+H)$^+$], and trans-N-((3RS,4SR)-4-cyclobutylamino-tetrahydro-pyran-3-yl)-2-methoxy-6-methylsulfanyl-4-trifluoromethyl-benzamide, light brown solid, MS: m/e=419.2 [(M+H)$^+$], were prepared in accordance with the general method of example 1 and 2 from 2-methoxy-6-methylsulfanyl-N-(4-oxo-tetrahydro-pyran-3-yl)-4-trifluoromethyl-benzamide (intermediate C) and cyclobutylamine.

Example 5 and 6

(+)-2-Methoxy-6-methylsulfanyl-N-(4-pyrrolidin-1-yl-tetrahydro-pyran-3-yl)-4-trifluoromethyl-benzamide and (−)-2-Methoxy-6-methylsulfanyl-N-(4-pyrrolidin-1-yl-tetrahydro-pyran-3-yl)-4-trifluoromethyl-benzamide

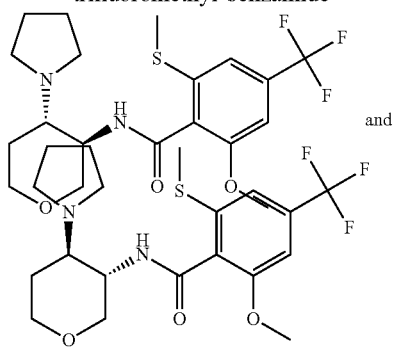

2-Methoxy-6-methylsulfanyl-N-((3RS,4SR)-4-pyrrolidin-1-yl-tetrahydro-pyran-3-yl)-4-trifluoromethyl-benzamide (example 2) was separated on Chiralpak AD with 15% ethanol in heptane. The first eluting enantiomer was (+)-2-methoxy-6-methylsulfanyl-N-(4-pyrrolidin-1-yl-tetrahydro-pyran-3-yl)-4-trifluoromethyl-benzamide, the second enantiomer was (−)-2-methoxy-6-methylsulfanyl-N-(4-pyrrolidin-1-yl-tetrahydro-pyran-3-yl)-4-trifluoromethyl-benzamide. The absolute stereochemistry was not determined.

Example 7

N-[(3RS,4SR)-4-(3-Hydroxy-pyrrolidin-1-yl)-tetrahydro-pyran-3-yl]-2-methoxy-6-methylsulfanyl-4-trifluoromethyl-benzamide

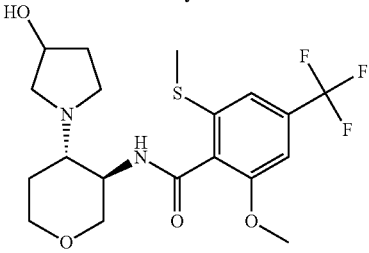

N-[(3RS,4SR)-4-(3-Hydroxy-pyrrolidin-1-yl)-tetrahydro-pyran-3-yl]-2-methoxy-6-methylsulfanyl-4-trifluoromethyl-benzamide, yellow solid, MS: m/e=435.3 [(M+H)$^+$], was prepared in accordance with the general method of example 1 and 2 from 2-methoxy-6-methylsulfanyl-N-(4-oxo-tetrahydro-pyran-3-yl)-4-trifluoromethyl-benzamide (intermediate C) and rac-3-pyrrolidinol.

Example 8

2-Cyclopropyl-N-((3SR,4RS)-4-pyrrolidin-1-yl-tetrahydro-pyran-3-yl)-4-trifluoromethyl-benzamide

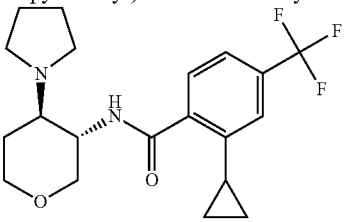

2-Cyclopropyl-4-trifluoromethyl-benzoic acid (intermediate J, 118 mg, 0.513 mmol) was dissolved in 2.5 mL dimethylformamide. N,N-Diisopropyl ethyl amine (338 mg, 2.62 mmol) and O-(7-azabenzotriazol-1-yl)-N,N,N',N'-tetramethyluronium hexafluorophosphate (195 mg, 0.513 mmol) were added. After 10 minutes of stirring at room temperature trans-(4-pyrrolidin-1-yl-tetrahydro-pyran-3-ylamine dihydrochloride (intermediate I, 187 mg, 0.769 mmol) was added. The reaction mixture was stirred at room temperature overnight. The solvent was evaporated off. The residue was taken up in 2N sodium carbonate solution and ethyl acetate and was extracted three times with ethyl acetate. The combined organic phases were dried on sodium sulfate, filtered and evaporated. Purification of the residue by flash chromatography on silica gel (heptane/ethyl acetate/triethylamine 1:0:0→10:10:1) yielded the title compound as a white solid (121 mg, 62%), MS: m/e=383.3 [(M+H)$^+$].

The following examples were prepared according to the method in example 8:

| Example Nr | Structure | Name | MS: m/e | Acid | Amine |
|---|---|---|---|---|---|
| 9 | 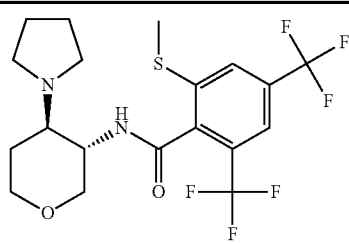 | 2-Methylsulfanyl-N-((3SR,4RS)-4-pyrrolidin-1-yl-tetrahydro-pyran-3-yl)-4,6-bis-trifluoromethyl-benzamide | 457.3 [(M + H)$^+$] | 2-Methyl-thio-4,6-bis(trifluoromethyl)benzoic acid (CAS 896120-49-3) | trans-(4-Pyrrolidin-1-yl-tetrahydro-pyran-3-ylamine dihydrochloride (intermediate I) |

-continued

| Example Nr | Structure | Name | MS: m/e | Acid | Amine |
|---|---|---|---|---|---|
| 10 | 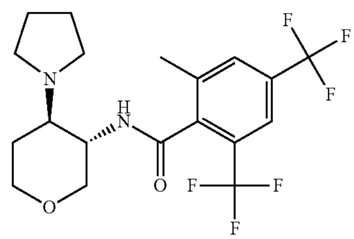 [SMILES: Cc1cc(C(F)(F)F)cc(C(F)(F)F)c1C(=O)N[C@@H]1COCC[C@H]1N1CCCC1] | 2-Methyl-N-((3SR,4RS)-4-pyrrolidin-1-yl-tetrahydro-pyran-3-yl)-4,6-bis-trifluoromethyl-benzamide | 425.2 [(M + H)+] | 2-methyl-4,6-bis(trifluoromethyl)benzoic acid (CAS 895580-37-7) | trans-(4-Pyrrolidin-1-yl-tetrahydro-pyran-3-ylamine dihydrochloride (intermediate I) |
| 11 | 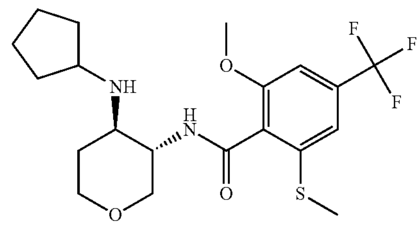 [SMILES: COc1cc(C(F)(F)F)cc(SC)c1C(=O)N[C@@H]1COCC[C@H]1NC1CCCC1] | N-((3SR,4RS)-4-Cyclopentylamino-tetrahydro-pyran-3-yl)-2-methoxy-6-methylsulfanyl-4-trifluoromethyl-benzamide | 433.4 [(M + H)+] | 2-Methoxy-6-methylsulfanyl-4-trifluoromethyl-benzoic acid (intermediate A) | trans-N-4-Cyclopentyl-tetrahydro-pyran-3,4-diamine dihydrochloride (intermediate L) |
| 12 | 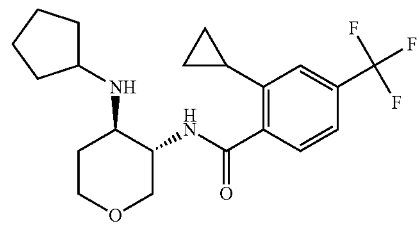 [SMILES: O=C(N[C@@H]1COCC[C@H]1NC1CCCC1)c1ccc(C(F)(F)F)cc1C1CC1] | N-((3SR,4RS)-4-Cyclopentylamino-tetrahydro-pyran-3-yl)-2-cyclopropyl-4-trifluoromethyl-benzamide | 397.3 [(M + H)+] | 2-Cyclopropyl-4-trifluoromethyl-benzoic acid (intermediate J) | trans-N-4-Cyclopentyl-tetrahydro-pyran-3,4-diamine dihydrochloride (intermediate L) |
| 13 | 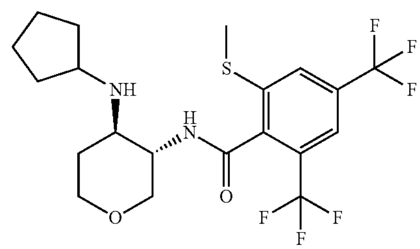 [SMILES: CSc1cc(C(F)(F)F)cc(C(F)(F)F)c1C(=O)N[C@@H]1COCC[C@H]1NC1CCCC1] | N-((3SR,4RS)-4-Cyclopentylamino-tetrahydro-pyran-3-yl)-2-methylsulfanyl-4,6-bis-trifluoromethyl-benzamide | 471.4 [(M + H)+] | 2-Methylthio-4,6-bi(trifluoromethyl)benzoic acid (CAS 896120-49-3) | trans-N-4-Cyclopentyl-tetrahydro-pyran-3,4-diamine dihydrochloride (intermediate L) |
| 14 | 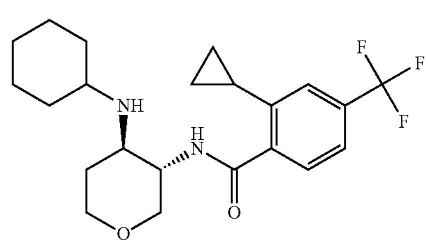 [SMILES: O=C(N[C@@H]1COCC[C@H]1NC1CCCCC1)c1ccc(C(F)(F)F)cc1C1CC1] | N-((3SR,4RS)-4-Cyclohexylamino-tetrahydro-pyran-3-yl)-2-cyclopropyl-4-trifluoromethyl-benzamide | 411.4 [(M + H)+] | 2-Cyclopropyl-4-trifluoromethyl-benzoic acid (intermediate J) | trans-N,4-cyclohexyl-tetrahydro-pyran-3,4-diamine hydrochloride (Intermediate Q) |
| 15 | 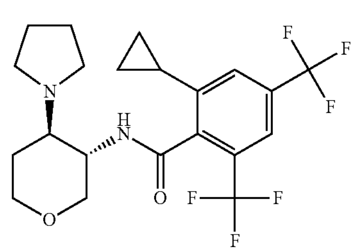 [SMILES: O=C(N[C@@H]1COCC[C@H]1N1CCCC1)c1c(C2CC2)cc(C(F)(F)F)cc1C(F)(F)F] | 2-Cyclopropyl-N-((3SR,4RS)-4-pyrrolidin-1-yl-tetrahydro-pyran-3-yl)-4,6-bis-trifluoromethyl-benzamide | 451.2 [(M + H)+] | 2-Cyclopropyl-4,6-bis-trifluoromethyl-benzoic acid (intermediate P) | trans-(4-Pyrrolidin-1-yl-tetrahydro-pyran-3-ylamine dihydrochloride (intermediate I) |

-continued

| Example Nr | Structure | Name | MS: m/e | Acid | Amine |
|---|---|---|---|---|---|
| 16 | 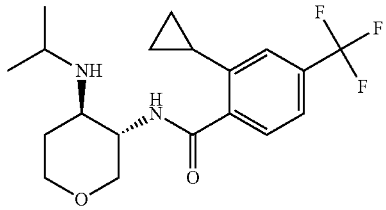 [SMILES: CC(C)N[C@@H]1CCOC[C@H]1NC(=O)c1ccc(C(F)(F)F)cc1C1CC1] | Cyclopropyl-N-((3SR,4RS)-4-isopropylamino-tetrahydro-pyran-3-yl)-4-trifluoro-methylbenzamide | 371.2 [(M + H)+] | 2-Cyclopropyl-4-trifluoro-methyl-benzoic acid (intermediate J) | trans-N-4-Isopropyl-tetrahydro-pyran-3,4-diamine hydrochloride (Intermediate R) |
| 17 | 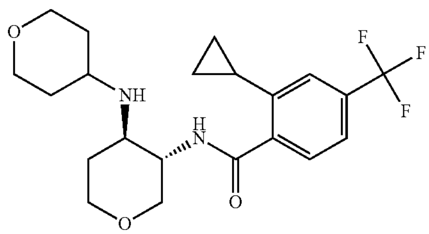 [SMILES: O=C(N[C@@H]1COCC[C@H]1NC1CCOCC1)c1ccc(C(F)(F)F)cc1C1CC1] | 2-Cyclopropyl-N-[(3SR,4RS)-4-(tetrahydro-pyran-4-ylamino)-tetrahydro-pyran-3-yl]-4-trifluoro-methylbenzamide | 413.3 [(M + H)+] | 2-Cyclopropyl-4-trifluoro-methyl-benzoic acid (intermediate J) | trans-N-4-(Tetrahydro-pyran-4-yl)-tetrahydro-pyran-3,4-diamine (Intermediate S) |
| 18 | 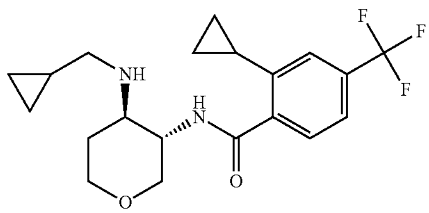 [SMILES: O=C(N[C@@H]1COCC[C@H]1NCC1CC1)c1ccc(C(F)(F)F)cc1C1CC1] | Cyclopropyl-N-[(3SR,4RS)-4-(cyclopropyl-methyl-amino)-tetrahydro-pyran-3-yl]-4-trifluoro-methylbenzamide | 383.3 [(M + H)+] | 2-Cyclopropyl-4-trifluoro-methyl-benzoic acid (intermediate J) | trans-N-4-Cyclopropyl-methyltetrahydro-pyran-3,4-diamine (Intermediate T) |
| 19 | 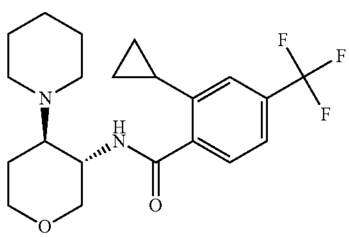 [SMILES: O=C(N[C@@H]1COCC[C@H]1N1CCCCC1)c1ccc(C(F)(F)F)cc1C1CC1] | 2-Cyclopropyl-N-((3SR,4RS)-4-piperidin-1-yl-tetrahydro-pyran-3-yl)-4-trifluoro-methylbenzamide | 397.2 [(M + H)+] | 2-Cyclopropyl-4-trifluoro-methyl-benzoic acid (intermediate J) | trans-4-Piperidin-1-yl-tetrahydro-pyran-3-yl-amine dihydrochloride (Intermediate U) |
| 20 | 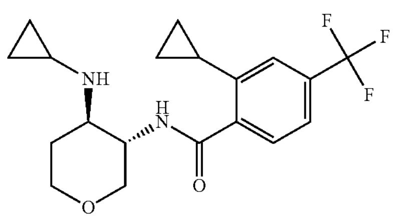 [SMILES: O=C(N[C@@H]1COCC[C@H]1NC1CC1)c1ccc(C(F)(F)F)cc1C1CC1] | 2-Cyclopropyl-N-((3SR,4RS)-4-cyclopropylamino-tetrahydro-pyran-3-yl)-4-trifluoromethyl-benzamide | 369.2 [(M + H)+] | 2-Cyclopropyl-4-trifluoro-methyl-benzoic acid (intermediate J) | trans-N-4-Cyclopropyl-tetrahydro-pyran-3,4-diamine dihydrochloride (Intermediate V) |
| 21 | 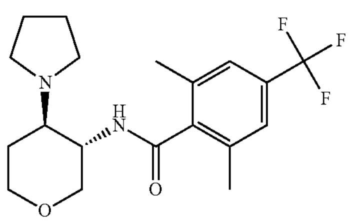 [SMILES: Cc1cc(C(F)(F)F)cc(C)c1C(=O)N[C@@H]1COCC[C@H]1N1CCCC1] | 2,6-Dimethyl-N-((3SR,4RS)-4-pyrrolidin-1-yl-tetrahydro-pyran-3-yl)-4-trifluoro-methylbenzamide | 371.2 [(M + H)+] | 2,6-Dimethyl-4-trifluoro-methyl-benzoic acid (Intermediate AD) | trans-(4-Pyrrolidin-1-yl-tetrahydro-pyran-3-ylamine dihydrochloride (intermediate I) |
| 22 | 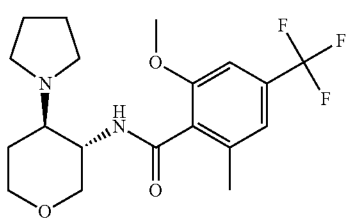 [SMILES: COc1cc(C(F)(F)F)cc(C)c1C(=O)N[C@@H]1COCC[C@H]1N1CCCC1] | 2-Methoxy-6-methyl-N-((3SR,4RS)-4-pyrrolidin-1-yl-tetrahydro-pyran-3-yl)-4-trifluoro-methylbenzamide | 387.2 [(M + H)+] | 2-Methoxy-6-methyl-4-trifluoromethyl-benzoic acid (Intermediate AE) | trans-(4-Pyrrolidin-1-yl-tetrahydro-pyran-3-ylamine dihydrochloride (intermediate I) |

-continued

| Example Nr | Structure | Name | MS: m/e | Acid | Amine |
|---|---|---|---|---|---|
| 23 | 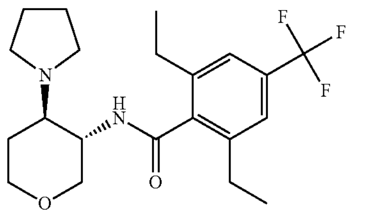 | 2,6-Diethyl-N-((3SR,4RS)-4-pyrrolidin-1-yl-tetrahydro-pyran-3-yl)-4-trifluoro-methylbenzamide | 399.2 [(M + H)+] | 2,6-Diethyl-4-trifluoromethyl-benzoic acid (Intermediate AF) | trans-(4-Pyrrolidin-1-yl-tetrahydro-pyran-3-ylamine dihydrochloride (intermediate I) |
| 24 | 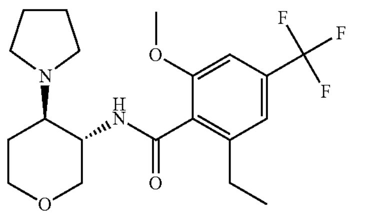 [SMILES: CCc1cc(C(F)(F)F)cc(OC)c1C(=O)N[C@@H]1COCC[C@H]1N1CCCC1] | 2-Ethyl-6-methoxy-N-((3SR,4RS)-4-pyrrolidin-1-yl-tetrahydro-pyran-3-yl)-4-trifluoro-methyl-benzamide | 401.3 [(M + H)+] | 2-Ethyl-6-methoxy-4-trifluoromethyl-benzoic acid (Intermediate AG) | trans-(4-Pyrrolidin-1-yl-tetrahydro-pyran-3-ylamine dihydrochloride (intermediate I) |
| 25 | 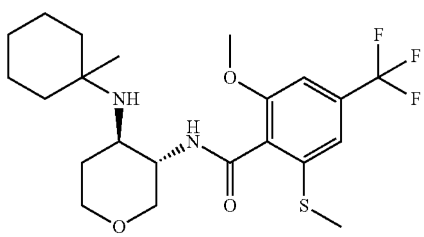 [SMILES: COc1cc(C(F)(F)F)cc(SC)c1C(=O)N[C@@H]1COCC[C@H]1NC1(C)CCCCC1] | 2-Methoxy-N-[(3SR,4RS)-4-(1-methyl-cyclohexyl-amino)-tetrahydro-pyran-3-yl]-6-methyl-sulfanyl-4-trifluoromethyl-benzamide | 461.4 [(M + H)+] | 2-Methoxy-6-methyl-sulfanyl-4-trifluoro-methyl-benzoic acid (intermediate A) | trans-N-4-(1-Methyl-cyclohexyl)-tetrahydro-pyran-3,4-diamine dihydrochloride (intermediate X) |
| 26 | 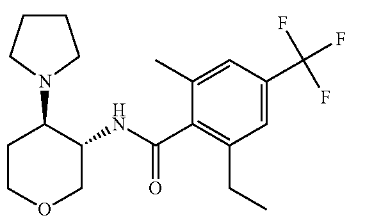 [SMILES: CCc1cc(C(F)(F)F)cc(C)c1C(=O)N[C@@H]1COCC[C@H]1N1CCCC1] | 2-Ethyl-6-methyl-N-((3SR,4RS)-4-pyrrolidin-1-yl-tetrahydro-pyran-3-yl)-4-trifluoro-methyl-benzamide | 385.2 [(M + H)+] | 2-Ethyl-6-methyl-4-trifluoromethyl-benzoic acid (Intermediate AH) | trans-(4-Pyrrolidin-1-yl-tetrahydro-pyran-3-ylamine dihydrochloride (intermediate I) |
| 27 | 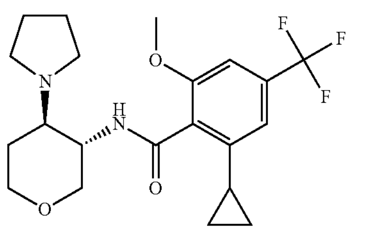 [SMILES: COc1cc(C(F)(F)F)cc(C2CC2)c1C(=O)N[C@@H]1COCC[C@H]1N1CCCC1] | Cyclopropyl-6-methoxy-N-((3SR,4RS) 4 pyrrolidin-1-yl-tetrahydro-pyran-3-yl)-4-trifluoro-methyl-benzamide | 413.3 [(M + H)+] | 2-Cyclopropyl-6-methoxy-4-trifluoromethyl-benzoic acid (Intermediate AI) | trans-(4-Pyrrolidin-1-yl-tetrahydro-pyran-3-ylamine dihydrochloride (intermediate I) |
| 28 | 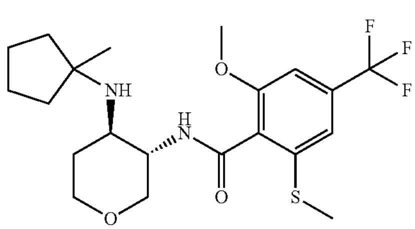 [SMILES: COc1cc(C(F)(F)F)cc(SC)c1C(=O)N[C@@H]1COCC[C@H]1NC1(C)CCCC1] | 2-Methoxy-N-[(3SR,4RS)-4-(1-methyl-cyclo-pentylamino)-tetrahydro-pyran-3-yl]-6-methyl-sulfanyl-4-trifluoromethyl-benzamide | 447.3 [(M + H)+] | 2-Methoxy-6-methylsulfanyl-4-trifluoro-methyl-benzoic acid (intermediate A) | trans-N-4-(1-Methyl-cyclopentyl)-tetrahydro-pyran-3,4-diamine hydrochloride (Intermediate Y) |
| 29 | 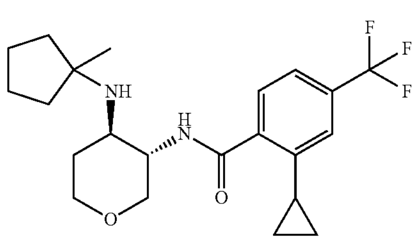 [SMILES: CC1(N[C@@H]2CCOC[C@H]2NC(=O)c2ccc(C(F)(F)F)cc2C2CC2)CCCC1] | 2-Cyclopropyl-N-[(3SR,4RS)-4-(1-methyl-cyclo-pentyl-amino)tetra-hydro-pyran-3-yl]-4-trifluoromethyl-benzamide | 411.4 [(M + H)+] | 2-Cyclopropyl-4-trifluoro-methyl-benzoic acid (intermediate J) | trans-N-4-(1-Methyl-cyclopentyl)tetrahydro-pyran-3,4-diamine hydrochloride (Intermediate Y) |

-continued

| Example Nr | Structure | Name | MS: m/e | Acid | Amine |
|---|---|---|---|---|---|
| 30 | 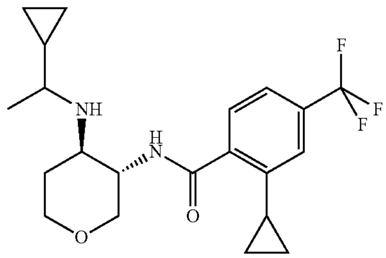 [SMILES: CC(N[C@@H]1CCOC[C@H]1NC(=O)c1ccc(C(F)(F)F)cc1C1CC1)C1CC1] | 2-Cyclopropyl-N-[(3RS,4SR)-4-(1-cyclopropyl-ethylamino)-tetrahydro-pyran-3-yl]-4-trifluoro-methylbenzamide | 397.2 [(M + H)+] | 2-Cyclopropyl-4-trifluoro-methyl-benzoic acid (intermediate J) | trans-N-4-(1-Cyclopropyl-ethyl)-tetrahydro-pyran-3,4-diamine dihydrochloride (Intermediate Z) |
| 31 | 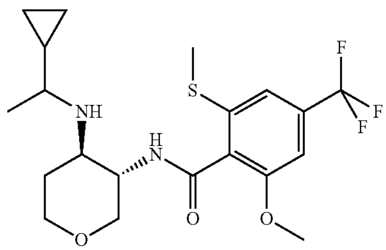 [SMILES: COc1cc(C(F)(F)F)cc(SC)c1C(=O)N[C@@H]1COCC[C@H]1NC(C)C1CC1] | N-[(3SR,4RS)-4-(1-Cyclopropyl-ethylamino)-tetrahydro-pyran-3-yl]-2-methoxy-6-methylsulfanyl-4-trifluoro-methyl-benzamide | 433.4 [(M + H)+] | 2-Methoxy-6-methylsulfanyl-4-trifluoro-methyl-benzoic acid (intermediate A) | trans-N-4-(1-Cyclopropyl-ethyl)-tetrahydro-pyran-3,4-diamine dihydrochloride (Intermediate Z) |
| 32 | 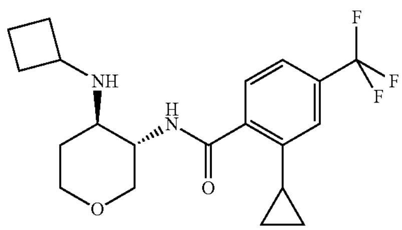 [SMILES: O=C(N[C@@H]1COCC[C@H]1NC1CCC1)c1ccc(C(F)(F)F)cc1C1CC1] | N-((3SR,4RS)-4-Cyclobutylamino-tetrahydro-pyran-3-yl)-2-cyclo-propyl-4-trifluoromethyl-benzamide | 383.3 [(M + H)+] | 2-Cyclopropyl-4-trifluoro-methyl-benzoic acid (intermediate J) | trans-N-4-Cyclobutyl-tetrahydro-pyran-3,4-diamine dihydrochloride (Intermediate AA) |
| 33 | 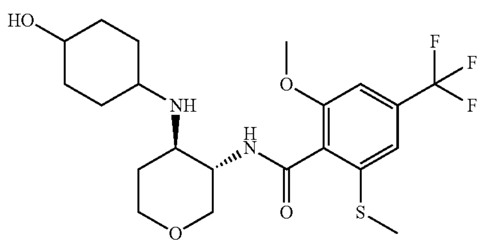 [SMILES: COc1cc(C(F)(F)F)cc(SC)c1C(=O)N[C@@H]1COCC[C@H]1NC1CCC(O)CC1] | N-[(3SR,4RS)-4-(4-Hydroxy-cyclohexylamino)-tetrahydro-pyran-3-yl]-2-methoxy-6-methylsulfanyl-4-trifluoromethyl-benzamide | 463.3 [(M + H)+] | 2-Methoxy-6-methylsulfanyl-4-trifluoro-methyl-benzoic acid (intermediate A) | trans-4-3-Amino-tetrahydro-pyran-4-ylamino)-cyclohexanol dihydrochloride (Intermediate AB) |
| 34 | 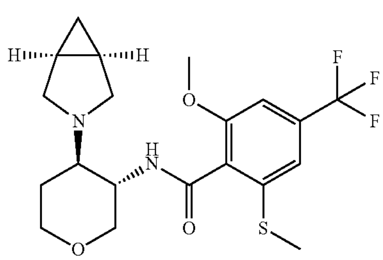 [SMILES: COc1cc(C(F)(F)F)cc(SC)c1C(=O)N[C@@H]1COCC[C@H]1N1C[C@H]2C[C@H]2C1] | N-[(3S,4R)-4-(3-Aza-bicyclo[3.1.0]hex-3-yl)-tetra-hydro-pyran-3-yl]-2-methoxy-6-methylsulfanyl-4-trifluoromethyl-benzamide | 431.2 [(M + H)+] | 2-Methoxy-6-methylsulfanyl-4-trifluoro-methyl-benzoic acid (intermediate A) | trans-4-(3-Aza-bicyclo[3.1.0]hex-3-yl)-tetrahydro-pyran-3-ylamine dihydrochloride (Intermediate AC) |
| 35 | 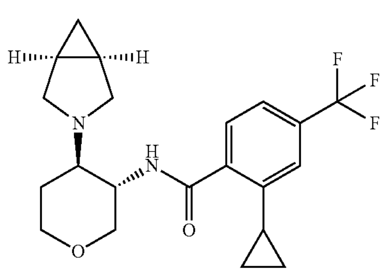 [SMILES: O=C(N[C@@H]1COCC[C@H]1N1C[C@H]2C[C@H]2C1)c1ccc(C(F)(F)F)cc1C1CC1] | N-[(3S,4R)-4-(3-Aza-bicyclo[3.1.0]hex-3-yl)-tetra-hydro-pyran-3-yl]-2-cyclopropyl-4-trifluoromethyl-benzamide | 395.1 [(M + H)+] | 2-Cyclopropyl-4-trifluoro-methyl-benzoic acid (intermediate J) | trans-4-(3-Aza-bicyclo[3.1.0]hex-3-yl)-tetrahydro-pyran-3-ylamine dihydrochloride (Intermediate AC) |

Example 36

2-Cyclopropyl-N-(3SR,4RS)-4-(4-hydroxy-piperidin-1-yl)-tetrahydro-pyran-3-yl]-4-trifluoromethyl-benzamide

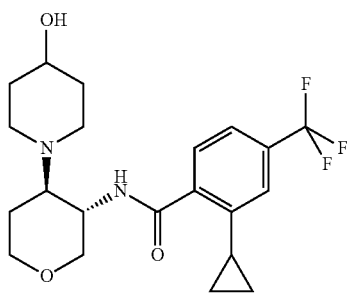 [SMILES: O=C(N[C@@H]1COCC[C@H]1N1CCC(O)CC1)c1ccc(C(F)(F)F)cc1C1CC1]

Step 1: Preparation of (3SR,4RS)-4-(4-oxo-piperidin-1-yl)-tetrahydro-pyran-3-yl]-carbamic acid tert-butyl ester

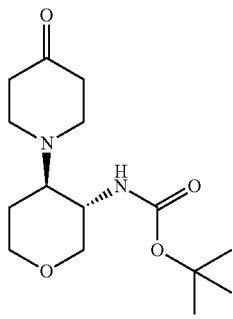 [SMILES: CC(C)(C)OC(=O)N[C@@H]1COCC[C@H]1N1CCC(=O)CC1]

To a solution of 100 mg (0.462 mmol) trans-(4-amino-tetrahydro-pyran-3-yl)-carbamic acid tert-butyl ester (Intermediate G) in 3 ml ethanol was added 51 mg (0.37 mmol) potassium carbonate. The mixture was refluxed in a 90° C. oil bath. A solution of 187 mg (0.693 mmol) 1-ethyl-1-methyl-4-oxo-piperidinium iodide in 1 ml water was added dropwise over a period of 30 minutes. The mixture was refluxed for 45 minutes, cooled to room temperature and diluted with water. The aqueous layer was extracted 3 times with dichloromethane. The combined extracts were dried over sodium sulfate, filtered and concentrated in vacuo. The crude product was purified with flash column chromatography on silica eluting with a gradient formed from n-heptane and ethyl acetate (0 to 50%) to provide 100 mg (yield: 73%) of the title compound as a white solid. MS (m/e): 299.5 (M+H$^+$).

Step 2: Preparation of 1-((3SR,4RS)-3-Amino-tetrahydro-pyran-4-yl)-piperidin-4-one hydrochloride

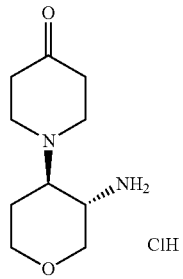 [SMILES: N[C@@H]1COCC[C@H]1N1CCC(=O)CC1 ; Cl]

The title compound, white solid, MS: m/e=199.3 [(M+H)$^+$], was prepared following procedure described for intermediate L from (3SR,4RS)-4-(4-oxo-piperidin-1-yl)-tetrahydro-pyran-3-yl]-carbamic acid tert-butyl ester

Step 3: Preparation of 2-cyclopropyl-N-(3RS,4SR)-4-(4-oxo-piperidin-1-yl)-tetrahydro-pyran-3-yl]-4-trifluoromethyl-benzamide

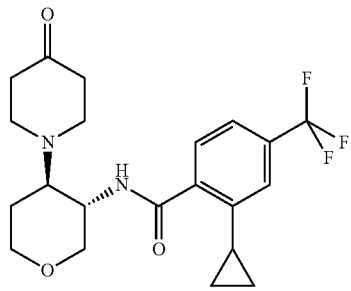 [SMILES: O=C1CCN([C@@H]2CCOC[C@H]2NC(=O)c2ccc(C(F)(F)F)cc2C2CC2)CC1]

The title compound, pale solid, MS: m/e=411.3 [(M+H)$^+$], was prepared in accordance with the general method of example 8 from 1-((3SR,4RS)-amino-tetrahydro-pyran-4-yl)-piperidin-4-one hydrochloride and 2-cyclopropyl-4-trifluoromethyl-benzoic acid (intermediate J)

Step 4: Preparation of 2-cyclopropyl-N-(3SR,4RS)-4-(4-hydroxy-piperidin-1-yl)-tetrahydro-pyran-3-yl]-4-trifluoromethyl-benzamide To a 10-20° C. stirring solution of 2-cyclopropyl-N-(3RS,4SR)-4-(4-oxo-piperidin-1-yl)-tetrahydro-pyran-3-yl]-4-trifluoromethyl-benzamide (73 mg) in ethanol (1.8 mL) was added sodium borohydride (13.5 mg) and the solution was stirred for 30 min. The reaction mixture was allowed to warm to room temperature, stirred for a further 3 hours and concentrated in vacuo. The resulting residue was partitioned between water and dichloromethane. The aqueous phase was washed three times with dichloromethane, and the combined organic phases were washed with brine, dried over sodium sulfate and concentrated in vacuo. The crude product was purified with flash column chromatography on silica eluting with a gradient formed from n-heptane and ethyl acetate (0 to 100%) to provide 44 mg (yield: 60%) of the title compound as a white solid. MS (m/e): 413.3 (M+H$^+$).

The following examples were prepared by separation on chiral HPLC:

| Expl Nr | Structure | Name | Racemate expl Nr | Chiral Column | Solvent | Retention time |
|---|---|---|---|---|---|---|
| 37 | 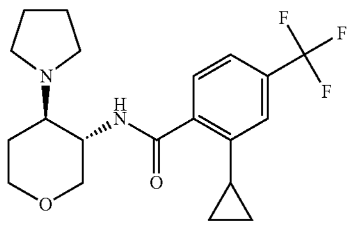 [SMILES: O=C(N[C@@H]1COCC[C@H]1N1CCCC1)c1ccc(C(F)(F)F)cc1C1CC1] | (+)-2-Cyclopropyl-N-(4-pyrrolidin-1-yl-tetrahydro-pyran-3-yl)-4-trifluoromethyl-benzamide | 8 | Chiralpak AD | 8% ethanol in heptane | 11 min |
| 38 | 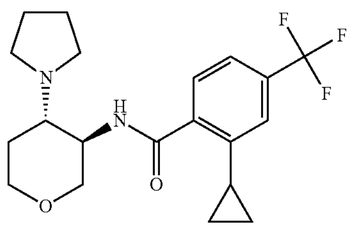 [SMILES: O=C(N[C@H]1COCC[C@@H]1N1CCCC1)c1ccc(C(F)(F)F)cc1C1CC1] | (−)-2-Cyclopropyl-N-(4-pyrrolidin-1-yl-tetrahydro-pyran-3-yl)-4-trifluoromethyl-benzamide | 8 | Chiralpak AD | 8% ethanol in heptane | 15 min |
| 39 | 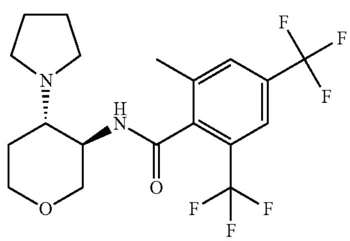 [SMILES: Cc1cc(C(F)(F)F)cc(C(F)(F)F)c1C(=O)N[C@H]1COCC[C@@H]1N1CCCC1] | (+)-2-Methyl-N-trans-(4-pyrrolidin-1-yl-tetrahydro-pyran-3-yl)-4,6-bis-trifluoro-methyl-benzamide | 10 | Chiralpak AD | 5% isopropanol in heptane | 63 min |
| 40 | 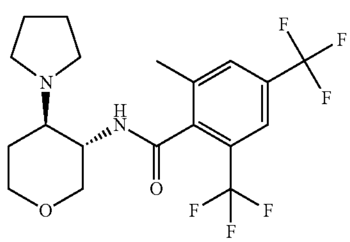 [SMILES: Cc1cc(C(F)(F)F)cc(C(F)(F)F)c1C(=O)N[C@@H]1COCC[C@H]1N1CCCC1] | (−)-2-Methyl-N-trans-(4-pyrrolidin-1-yl-tetrahydro-pyran-3-yl)-4,6-bis-trifluoromethyl-benzamide | 10 | Chiralpak AD | 5% isopropanol in heptane | 77 min |
| 41 | 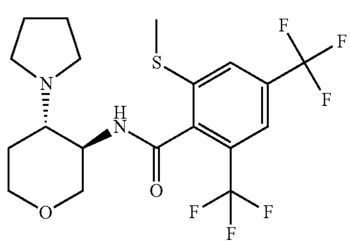 [SMILES: CSc1cc(C(F)(F)F)cc(C(F)(F)F)c1C(=O)N[C@H]1COCC[C@@H]1N1CCCC1] | (+)-2-Methylsulfanyl-N-trans-(4-pyrrolidin-1-yl-tetrahydro-pyran-3-yl)-4,6-bis-trifluoromethyl-benzamide | 9 | Chiralpak AD | 5% ethanol in heptane | 58 min |
| 42 | 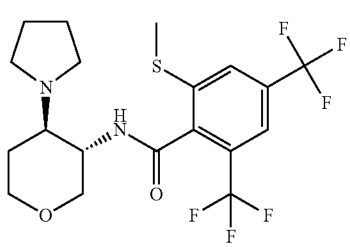 [SMILES: CSc1cc(C(F)(F)F)cc(C(F)(F)F)c1C(=O)N[C@@H]1COCC[C@H]1N1CCCC1] | (−)-2-Methylsulfanyl-N-trans-(4-pyrrolidin-1-yl-tetrahydro-pyran-3-yl)-4,6-bis-trifluoromethyl-benzamide | 9 | Chiralpak AD | 5% ethanol in heptane | 67 min |

-continued

| Expl Nr | Structure | Name | Racemate expl Nr | Chiral Column | Solvent | Retention time |
|---|---|---|---|---|---|---|
| 43 | 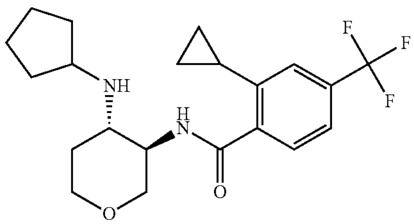 [SMILES: O=C(N[C@H]1COCC[C@@H]1NC1CCCC1)c1ccc(C(F)(F)F)cc1C1CC1] | (+)-N-(trans-4-Cyclopentylamino-tetrahydro-pyran-3-yl)-2-cyclopropyl-4-trifluoromethyl-benzamide | 12 | Chiralpak AD | 10% isopropanol in heptane | 10 min |
| 44 | 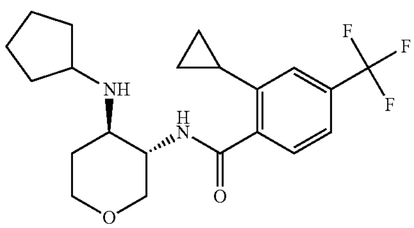 [SMILES: O=C(N[C@@H]1COCC[C@H]1NC1CCCC1)c1ccc(C(F)(F)F)cc1C1CC1] | (−)-N-(trans-4-Cyclopentylamino-tetrahydro-pyran-3-yl)-2-cyclopropyl-4-trifluoromethyl-benzamide | 12 | Chiralpak AD | 10% isopropanol in heptane | 12 min |
| 45 | 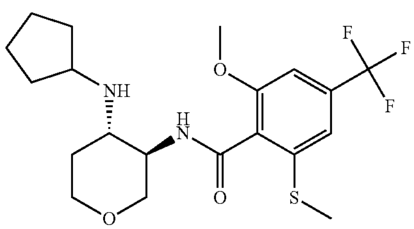 [SMILES: COc1cc(C(F)(F)F)cc(SC)c1C(=O)N[C@H]1COCC[C@@H]1NC1CCCC1] | (+)-N-(4-Cyclopentylamino-tetrahydro-pyran-3-yl)-2-methoxy-6-methylsulfanyl-4-trifluoromethyl-benzamide | 11 | Chiralpak AD | 12% isopropanol in heptane | 10 min |
| 46 | 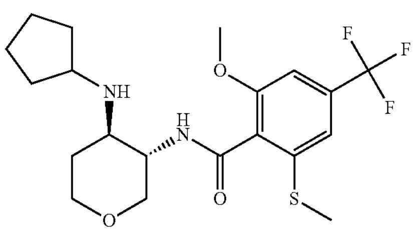 [SMILES: COc1cc(C(F)(F)F)cc(SC)c1C(=O)N[C@@H]1COCC[C@H]1NC1CCCC1] | (−)-N-(4-Cyclopentylamino-tetrahydro-pyran-3-yl)-2-methoxy-6-methylsulfanyl-4-trifluoromethyl-benzamide | 11 | Chiralpak AD | 12% isopropanol in heptane | 13 min |
| 47 | 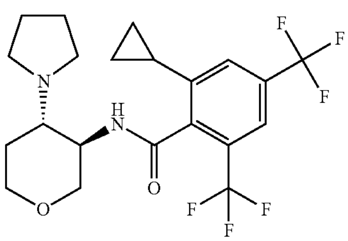 [SMILES: O=C(N[C@H]1COCC[C@@H]1N1CCCC1)c1c(C2CC2)cc(C(F)(F)F)cc1C(F)(F)F] | (+)-2-Cyclopropyl-N-(4-pyrrolidin-1-yl-tetrahydro-pyran-3-yl)-4,6-bis-trifluoromethyl-benzamide | 15 | Chiralpak AD | 4% isopropanol in heptane | 8 min |
| 48 | 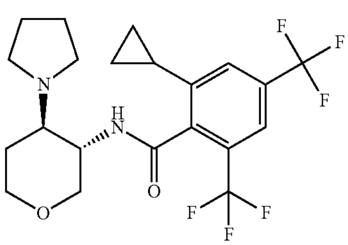 [SMILES: O=C(N[C@@H]1COCC[C@H]1N1CCCC1)c1c(C2CC2)cc(C(F)(F)F)cc1C(F)(F)F] | (−)-2-Cyclopropyl-N-(4-pyrrolidin-1-yl-tetrahydro-pyran-3-yl)-4,6-bis-trifluoromethyl-benzamide | 15 | Chiralpak AD | 4% isopropanol in heptane | 15 min |

-continued

| Expl Nr | Structure | Name | Racemate expl Nr | Chiral Column | Solvent | Retention time |
|---|---|---|---|---|---|---|
| 49 | 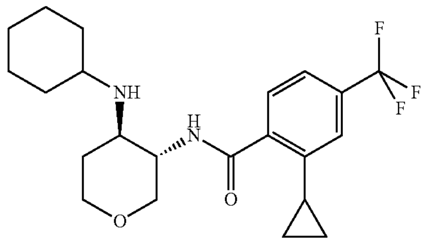 [SMILES: O=C(N[C@@H]1COCC[C@H]1NC1CCCCC1)c1ccc(C(F)(F)F)cc1C1CC1] | (−)-N-4-Cyclohexylamino-tetrahydro-pyran-3-yl)-2-cyclopropyl-4-trifluoromethyl-benzamide | 14 | Chiralpak AD | 4% isopropanol in heptane | 10 min |
| 50 | 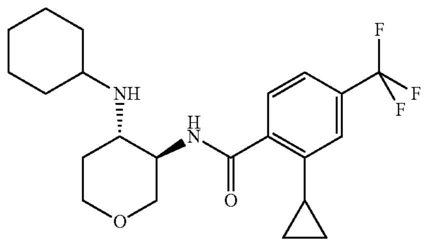 [SMILES: O=C(N[C@H]1COCC[C@@H]1NC1CCCCC1)c1ccc(C(F)(F)F)cc1C1CC1] | (+)-N-4-Cyclohexylamino-tetrahydro-pyran-3-yl)-2-cyclopropyl-4-trifluoromethyl-benzamide | 14 | Chiralpak AD | 4% isopropanol in heptane | 12 min |
| 51 | 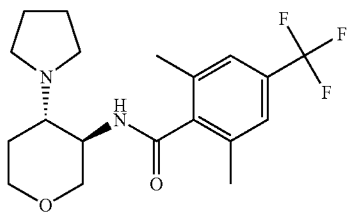 [SMILES: Cc1cc(C(F)(F)F)cc(C)c1C(=O)N[C@H]1COCC[C@@H]1N1CCCC1] | (+)-2,6-Dimethyl-N-4-pyrrolidin-1-yl-tetrahydro-pyran-3-yl)-4-trifluoromethyl-benzamide | 21 | Chiralpak AD | 4% isopropanol in heptane | 9 min |
| 52 | 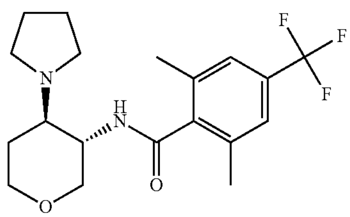 [SMILES: Cc1cc(C(F)(F)F)cc(C)c1C(=O)N[C@@H]1COCC[C@H]1N1CCCC1] | (−)-2,6-Dimethyl-N-4-pyrrolidin-1-yl-tetrahydro-pyran-3-yl)-4-trifluoromethyl-benzamide | 21 | Chiralpak AD | 4% isopropanol in heptane | 12 min |
| 53 | 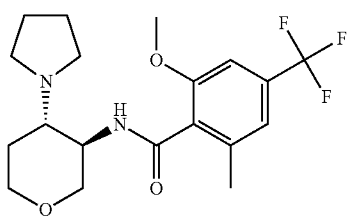 [SMILES: COc1cc(C(F)(F)F)cc(C)c1C(=O)N[C@H]1COCC[C@@H]1N1CCCC1] | (+)-2-Methoxy-6-methyl-N-(4-pyrrolidin-1-yl-tetrahydro-pyran-3-yl)-4-trifluoromethyl-benzamide | 22 | Chiralpak AD | 4% isopropanol in heptane | 9 min |
| 54 | 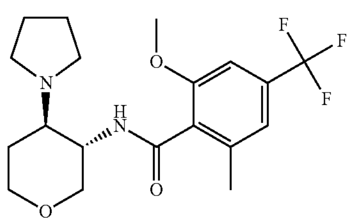 [SMILES: COc1cc(C(F)(F)F)cc(C)c1C(=O)N[C@@H]1COCC[C@H]1N1CCCC1] | (−)-2-Methoxy-6-methyl-N-4-pyrrolidin-1-yl-tetrahydro-pyran-3-yl)-4-trifluoro-methyl-benzamide | 22 | Chiralpak AD | 4% isopropanol in heptane | 13 min |
| 55 | 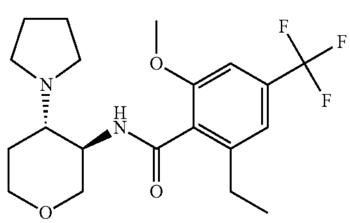 [SMILES: CCc1cc(C(F)(F)F)cc(OC)c1C(=O)N[C@H]1COCC[C@@H]1N1CCCC1] | (+)-2-Ethyl-6-methoxy-N-4-pyrrolidin-1-yl-tetrahydro-pyran-3-yl)-4-trifluoro-methyl-benzamide | 24 | Chiralpak AD | 4% isopropanol in heptane | 7 min |

-continued

| Expl Nr | Structure | Name | Racemate expl Nr | Chiral Column | Solvent | Retention time |
|---|---|---|---|---|---|---|
| 56 | 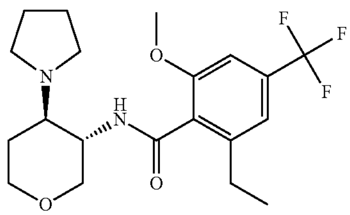 [SMILES: CCc1cc(C(F)(F)F)cc(OC)c1C(=O)N[C@@H]1COCC[C@H]1N1CCCC1] | (−)-2-Ethyl-6-methoxy-N-(4-pyrrolidin-1-yl-tetrahydro-pyran-3-yl)-4-trifluoro-methyl-benzamide | 24 | Chiralpak AD | 4% isopropanol in heptane | 13 min |
| 57 | 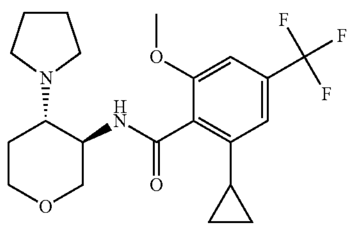 [SMILES: COc1cc(C(F)(F)F)cc(C2CC2)c1C(=O)N[C@H]1COCC[C@@H]1N1CCCC1] | (+)-2-Cyclopropyl-6-methoxy-N-4-pyrrolidin-1-yl-tetrahydro-pyran-3-yl)-4-trifluoro-methyl-benzamide | 27 | Chiralpak AD | 4% isopropanol in heptane | 9 min |
| 58 | 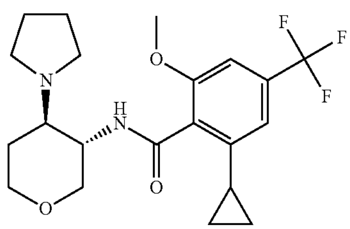 [SMILES: COc1cc(C(F)(F)F)cc(C2CC2)c1C(=O)N[C@@H]1COCC[C@H]1N1CCCC1] | (−)-2-Cyclopropyl-6-methoxy-N-4-pyrrolidin-1-yl-tetrahydro-pyran-3-yl)-4-trifluoro-methyl-benzamide | 27 | Chiralpak AD | 4% isopropanol in heptane | 19 min |
| 64 | 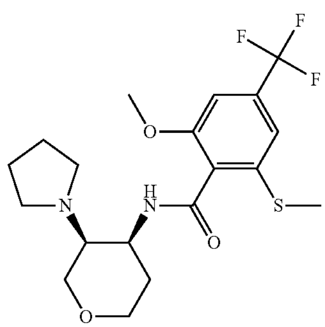 [SMILES: COc1cc(C(F)(F)F)cc(SC)c1C(=O)N[C@H]1CCOC[C@H]1N1CCCC1] | (−)-2-Methoxy-6-methylsulfanyl-N-(3-pyrrolidin-1-yl-tetrahydro-pyran-4-yl)-4-trifluoro-methyl-benzamide | 63 | Reprosil Chiral NR | 20% ethanol in heptane | 20 min |
| 65 | 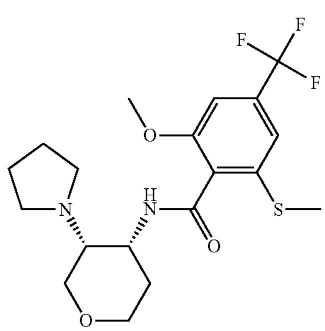 [SMILES: COc1cc(C(F)(F)F)cc(SC)c1C(=O)N[C@@H]1CCOC[C@@H]1N1CCCC1] | (+)-2-Methoxy-6-methylsulfanyl-N-(3-pyrrolidin-1-yl-tetrahydro-pyran-4-yl)-4-trifluoro-methyl-benzamide | 63 | Reprosil Chiral NR | 20% ethanol in heptane | 26 min |

Example 59

N-(3SR,4RS)-4-(2-Aza-bicyclo[3.1.0]hex-2-yl)-tetrahydro-pyran-3-yl]-2-methoxy-6-methylsulfanyl-4-trifluoromethyl-benzamide

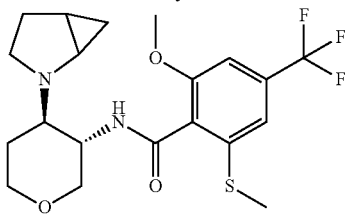

The title compound, yellow solid, MS: m/e=431.2 [(M+H)+], was prepared in accordance with the general method of example 8 from trans-4-(2-aza-bicyclo[3.1.0]hex-2-yl)-tetrahydro-pyran-3-ylamine hydrochloride-diastereoisomer 1 (Intermediate AJ) and 2-methoxy-6-methylsulfanyl-4-trifluoromethyl-benzoic acid (intermediate A).

Example 60

N-(3SR,4RS)-4-(2-Aza-bicyclo[3.1.0]hex-2-yl)-tetrahydro-pyran-3-yl]-2-methoxy-6-methylsulfanyl-4-trifluoromethyl-benzamide

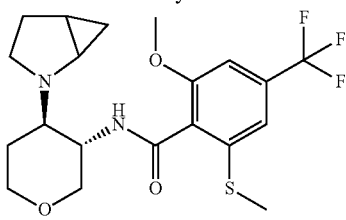

The title compound, yellow solid, MS: m/e=431.2 [(M+H)+], was prepared in accordance with the general method of example 8 trans-4-(2-aza-bicyclo[3.1.0]hex-2-yl)-tetrahydro-pyran-3-ylamine hydrochloride-diastereoisomer 2 (Intermediate AK) and 2-methoxy-6-methylsulfanyl-4-trifluoromethyl-benzoic acid (intermediate A)

Example 61

2-Cyclopropyl-N-(3RS,4SR)-4-(3-hydroxy-pyrrolidin-1-yl)-tetrahydro-pyran-3-yl]-4-trifluoromethyl-benzamide

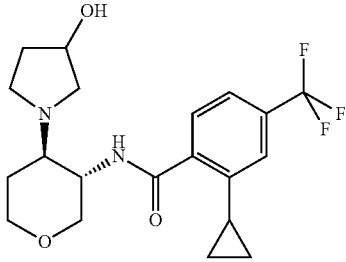 [SMILES: O=C(N[C@@H]1COCC[C@H]1N1CCC(O)C1)c1ccc(C(F)(F)F)cc1C1CC1]

The title compound, yellow solid, MS: m/e=399.2 [(M+H)+], was prepared in accordance with the general method of example 8 from trans-1-(3-amino-tetrahydro-pyran-4-yl)-pyrrolidin-3-ol dihydrochlorid-diastereoisomer 1 (Intermediate AL) and 2-cyclopropyl-4-trifluoromethyl-benzoic acid (intermediate J).

Example 62

2-Cyclopropyl-N-(3RS,4SR)-4-(3-hydroxy-pyrrolidin-1-yl)-tetrahydro-pyran-3-yl]-4-trifluoromethyl-benzamide

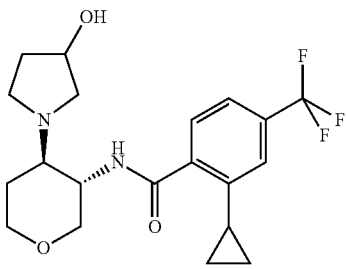 [SMILES: O=C(N[C@@H]1COCC[C@H]1N1CCC(O)C1)c1ccc(C(F)(F)F)cc1C1CC1]

The title compound, yellow solid, MS: m/e=399.2 [(M+H)+], was prepared in accordance with the general method of example 8 from trans-1-(3-amino-tetrahydro-pyran-4-yl)-pyrrolidin-3-ol dihydrochlorid-diastereoisomer 2 (Intermediate AM) and 2-cyclopropyl-4-trifluoromethyl-benzoic acid (intermediate J).

Example 63 cis-2-Methoxy-6-methylsulfanyl-N-(3-pyrrolidin-1-yl-tetrahydro-pyran-4-yl)-4-trifluoromethyl-benzamide

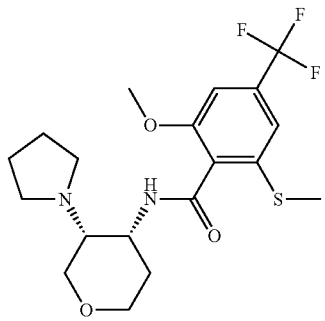 [SMILES: COc1cc(C(F)(F)F)cc(SC)c1C(=O)N[C@@H]1CCOC[C@@H]1N1CCCC1]

The title compound, brown solid, MS: m/e=419.3 [(M+H)+], was prepared in accordance with the general method of intermediate H from N-(3-amino-tetrahydro-pyran-4-yl)-2-methoxy-6-methylsulfanyl-4-trifluoromethyl-benzamide hydrochloride (intermediate AP) and 1,4-dibromopropane. The two diastereomers were separated by column chromatography.

The compounds of formula I and their pharmaceutically usable addition salts possess valuable pharmacological properties. Specifically, it has been found that the compounds of the present invention are good inhibitors of the glycine transporter I (GlyT-1).

The compounds were investigated in accordance with the test given hereinafter.

Solutions and materials

DMEM complete medium: Nutrient mixture F-12 (Gibco Life-technologies), fetal bovine serum (FBS) 5%, (Gibco life technologies), Penicillin/Streptomycin 1% (Gibco life technologies), Hygromycin 0.6 mg/ml (Gibco life technologies), Glutamine 1 mM Gibco life technologies)

Uptake buffer (UB): 150 mM NaCl, 10 mM Hepes-Tris, pH 7.4, 1 mM $CaCl_2$, 2.5 mM KCl, 2.5 mM $MgSO_4$, 10 mM (+) D-glucose.

Flp-in™-CHO (Invitrogen Cat no R758-07) cells stably transfected with mGlyT1b cDNA.

Glycine Uptake Inhibition Assay (mGlyT-1b)

On day 1 mammalian cells, (Flp-in™-CHO), transfected with mGlyT-1b cDNA, were plated at the density of 40,000 cells/well in complete F-12 medium, without hygromycin in 96-well culture plates. On day 2, the medium was aspirated and the cells were washed twice with uptake buffer (UB). The cells were then incubated for 20 min at 22° C. with either (i) no potential competitor, (ii) 10 mM non-radioactive glycine, (iii) a concentration of a potential inhibitor. A range of concentrations of the potential inhibitor was used to generate data for calculating the concentration of inhibitor resulting in 50% of the effect (e.g. $IC_{50}$, the concentration of the competitor inhibiting glycine uptake of 50%). A solution was then immediately added containing [$^3$H]-glycine 60 nM (11-16 Ci/mmol) and 25 µM non-radioactive glycine. The plates were incubated with gentle shaking and the reaction was stopped by aspiration of the mixture and washing (three times) with ice-cold UB. The cells were lysed with scintillation liquid, shaken 3 hours and the radioactivity in the cells was counted using a scintillation counter.

The compounds described in examples 1-60 have an $IC_{50}$ data<1.0 µM. The $IC_{50}$ data (<0.2 µM) for compounds 1-128 is be provided in table 1.

TABLE

| Example | $IC_{50}$ data (µM) |
|---|---|
| 1 | 0.2605 |
| 2 | 0.0662 |
| 3 | 0.5056 |
| 4 | 0.3375 |
| 5 | 0.1176 |
| 6 | 0.0284 |
| 7 | 0.1546 |
| 8 | 0.0363 |
| 9 | 0.0165 |
| 10 | 0.0412 |
| 11 | 0.1267 |
| 12 | 0.075 |
| 13 | 0.2503 |
| 14 | 0.1249 |
| 15 | 0.0132 |
| 16 | 0.2962 |
| 17 | 0.9039 |
| 18 | 0.1264 |
| 19 | 0.0815 |
| 20 | 0.1935 |
| 21 | 0.0452 |
| 22 | 0.1045 |
| 23 | 0.0584 |
| 24 | 0.0641 |
| 25 | 0.2775 |
| 26 | 0.0179 |
| 27 | 0.0147 |
| 28 | 0.1439 |
| 29 | 0.2349 |
| 30 | 0.0838 |
| 31 | 0.2756 |
| 32 | 0.1193 |
| 33 | 0.7514 |
| 34 | 0.1099 |
| 35 | 0.0265 |
| 36 | 0.2743 |
| 37 | 0.0834 |
| 38 | 0.0834 |
| 39 | 0.0439 |

TABLE-continued

| Example | $IC_{50}$ data (µM) |
|---|---|
| 40 | 0.0955 |
| 41 | 0.0447 |
| 42 | 0.027 |
| 43 | 0.0788 |
| 44 | 0.2989 |
| 45 | 0.111 |
| 46 | 0.1581 |
| 47 | 0.016 |
| 48 | 0.02 |
| 49 | 0.3398 |
| 50 | 0.057 |
| 51 | 0.0253 |
| 52 | 0.0341 |
| 53 | 0.0782 |
| 54 | 0.0338 |
| 55 | 0.0483 |
| 56 | 0.0155 |
| 57 | 0.0625 |
| 58 | 0.0076 |
| 59 | 0.1136 |
| 60 | 0.0264 |
| 61 | 0.3481 |
| 62 | 0.2819 |
| 63 | 0.1893 |
| 64 | 0.1893 |
| 65 | 0.1186 |

The invention provides pharmaceutical compositions containing compounds of formula I and their pharmaceutically acceptable salts in combination with pharmaceutically acceptable carriers. These pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, parenterally, e.g. in the form of injection solutions.

Pharmaceutically acceptable carriers include pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Pharmaceutical compositions containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

The most preferred indications in accordance with the present invention are those, which include disorders of the central nervous system, for example the treatment or prevention of schizophrenia, cognitive impairment and Alzheimer's disease.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of formula I or of the corresponding amount of a pharmaceutically acceptable salt thereof. The daily dosage can be administered as single dose or in divided doses and, in addition, the upper limit can also be exceeded when this is found to be indicated.

Tablet Formulation (Wet Granulation)

|      |                          | mg/tablet |       |        |        |
|------|--------------------------|-----------|-------|--------|--------|
| Item | Ingredients              | 5 mg      | 25 mg | 100 mg | 500 mg |
| 1.   | Compound of formula I    | 5         | 25    | 100    | 500    |
| 2.   | Lactose Anhydrous DTG    | 125       | 105   | 30     | 150    |
| 3.   | Sta-Rx 1500              | 6         | 6     | 6      | 30     |
| 4.   | Microcrystalline Cellulose | 30      | 30    | 30     | 150    |
| 5.   | Magnesium Stearate       | 1         | 1     | 1      | 1      |
|      | Total                    | 167       | 167   | 167    | 831    |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

|      |                       | mg/capsule |       |        |        |
|------|-----------------------|------------|-------|--------|--------|
| Item | Ingredients           | 5 mg       | 25 mg | 100 mg | 500 mg |
| 1.   | Compound of formula I | 5          | 25    | 100    | 500    |
| 2.   | Hydrous Lactose       | 159        | 123   | 148    | —      |
| 3.   | Corn Starch           | 25         | 35    | 40     | 70     |
| 4.   | Talc                  | 10         | 15    | 10     | 25     |
| 5.   | Magnesium Stearate    | 1          | 2     | 2      | 5      |
|      | Total                 | 200        | 200   | 300    | 600    |

Manufacturing Procedure
1. Mix items 1, 2 and 3 in a suitable mixer for 30 minutes.
2. Add items 4 and 5 and mix for 3 minutes.
3. Fill into a suitable capsule.

The invention claimed is:
1. A compound of formula I

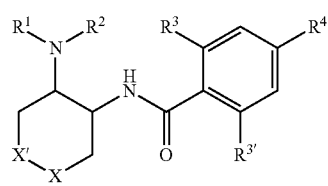

wherein $R^1$ and $R^2$ are each independently hydrogen, $(CR_2)_o$-cycloalkyl optionally substituted by lower alkyl or hydroxy, or are lower alkyl or heterocycloalkyl, o is 0 or 1; and each R is the same or different and is hydrogen or lower alkyl; or $R^1$ and $R^2$ together with the N atom to which they are attached form a heterocycloalkyl group, selected from the group consisting of pyrrolidinyl, piperidinyl, 3-aza-bicyclo[3.1.0]hex-3-yl and 2-aza-bicyclo[3.1.0]hex-2-yl, each of which is optionally substituted by hydroxy;

$R^3$ is S-lower alkyl, lower alkyl, lower alkoxy or cycloalkyl;

$R^{3'}$ is hydrogen, lower alkyl substituted by halogen, lower alkyl or lower alkoxy;

$R^4$ is lower alkyl substituted by halogen, lower alkyl or lower alkoxy;

X is —O— or —CH$_2$—; and

X' is —O— or —CH$_2$—; with the proviso that one of X or X' is always —O— and the other is —CH$_2$—;

or a pharmaceutically acceptable acid addition salt, racemic mixture, corresponding enantiomer or optical isomer thereof.

2. The compound of claim 1, having formula I-1,

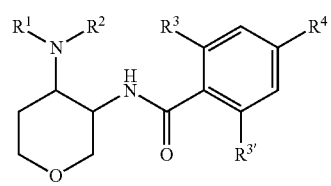

wherein $R^1$ and $R^2$ are each independently hydrogen, $(CR_2)_o$-cycloalkyl optionally substituted by lower alkyl or hydroxy, or are lower alkyl or heterocycloalkyl, o is 0 or 1; and each R is the same or different and is hydrogen or lower alkyl; or $R^1$ and $R^2$ together with the N atom to which they are attached form a heterocycloalkyl group, selected from the group consisting of pyrrolidinyl, piperidinyl, 3-aza-bicyclo[3.1.0]hex-3-yl and 2-aza-bicyclo[3.1.0]hex-2-yl, each of which is optionally substituted by hydroxy;

$R^3$ is S-lower alkyl, lower alkyl, lower alkoxy or cycloalkyl;

$R^{3'}$ is hydrogen, lower alkyl substituted by halogen, lower alkyl or lower alkoxy; and $R^4$ is lower alkyl substituted by halogen, lower alkyl or lower alkoxy;

or a pharmaceutically acceptable acid addition salt, racemic mixture, corresponding enantiomer or optical isomer thereof.

3. The compound of claim 2, wherein $R^1$ and $R^2$ together with the N atom to which they are attached form a heterocycloalkyl group, selected from the group consisting of pyrrolidinyl, piperidinyl, 3-aza-bicyclo[3.1.0]hex-3-yl and 2-aza-bicyclo[3.1.0]hex-2-yl, each of which is optionally substituted by hydroxy.

4. The compound of claim 3, selected from the group consisting of
2-methoxy-6-methylsulfanyl-N-((3RS,4SR)-4-pyrrolidin-1-yl-tetrahydro-pyran-3-yl)-4-trifluoromethyl-benzamide;
(−)-2-methoxy-6-methylsulfanyl-N-(4-pyrrolidin-1-yl-tetrahydro-pyran-3-yl)-4-trifluoromethyl-benzamide;
2-cyclopropyl-N-((3SR,4RS)-4-pyrrolidin-1-yl-tetrahydro-pyran-3-yl)-4-trifluoromethyl-benzamide;
2-methylsulfanyl-N-((3SR,4RS)-4-pyrrolidin-1-yl-tetrahydro-pyran-3-yl)-4,6-bis-trifluoromethyl-benzamide;
2-methyl-N-((3SR,4RS)-4-pyrrolidin-1-yl-tetrahydro-pyran-3-yl)-4,6-bis-trifluoromethyl-benzamide;
2-cyclopropyl-N-((3SR,4RS)-4-pyrrolidin-1-yl-tetrahydro-pyran-3-yl)-4,6-bis-trifluoromethyl-benzamide;
2-cyclopropyl-N-((3SR,4RS)-4-piperidin-1-yl-tetrahydro-pyran-3-yl)-4-trifluoromethyl-benzamide;
2,6-dimethyl-N-((3SR,4RS)-4-pyrrolidin-1-yl-tetrahydro-pyran-3-yl)-4-trifluoromethyl-benzamide;
2,6-diethyl-N-((3SR,4RS)-4-pyrrolidin-1-yl-tetrahydro-pyran-3-yl)-4-trifluoromethyl-benzamide; and
2-ethyl-6-methoxy-N-((3SR,4RS)-4-pyrrolidin-1-yl-tetrahydro-pyran-3-yl)-4-trifluoromethyl-benzamide.

5. The compound of claim 3, selected from the group consisting of
2-ethyl-6-methyl-N-((3SR,4RS)-4-pyrrolidin-1-yl-tetrahydro-pyran-3-yl)-4-trifluoromethyl-benzamide;
2-cyclopropyl-6-methoxy-N-((3SR,4RS)-4-pyrrolidin-1-yl-tetrahydro-pyran-3-yl)-4-trifluoromethyl-benzamide;
N-[(3S,4R)-4-(3-aza-bicyclo[3.1.0]hex-3-yl)-tetrahydro-pyran-3-yl]-2-cyclopropyl-4-trifluoromethyl-benzamide;
(+)-2-cyclopropyl-N-(4-pyrrolidin-1-yl-tetrahydro-pyran-3-yl)-4-trifluoromethyl-benzamide;
(−)-2-cyclopropyl-N-(4-pyrrolidin-1-yl-tetrahydro-pyran-3-yl)-4-trifluoromethyl-benzamide;
(+)-2-methyl-N-trans-(4-pyrrolidin-1-yl-tetrahydro-pyran-3-yl)-4,6-bis-trifluoromethyl-benzamide;
(−)-2-methyl-N-trans-(4-pyrrolidin-1-yl-tetrahydro-pyran-3-yl)-4,6-bis-trifluoromethyl-benzamide;
(+)-2-methylsulfanyl-N-trans-(4-pyrrolidin-1-yl-tetrahydro-pyran-3-yl)-4,6-bis-trifluoromethyl-benzamide;
(−)-2-methylsulfanyl-N-trans-(4-pyrrolidin-1-yl-tetrahydro-pyran-3-yl)-4,6-bis-trifluoromethyl-benzamide; and
(+)-2-cyclopropyl-N-(4-pyrrolidin-1-yl-tetrahydro-pyran-3-yl)-4,6-bis-trifluoromethyl-benzamide.

6. The compound of claim 3, selected from the group consisting of
(−)-2-cyclopropyl-N-(4-pyrrolidin-1-yl-tetrahydro-pyran-3-yl)-4,6-bis-trifluoromethyl-benzamide;
(+)-2,6-dimethyl-N-4-pyrrolidin-1-yl-tetrahydro-pyran-3-yl)-4-trifluoromethyl-benzamide;
(−)-2,6-Dimethyl-N-4-pyrrolidin-1-yl-tetrahydro-pyran-3-yl)-4-trifluoromethyl-benzamide;
(+)-2-methoxy-6-methyl-N-(4-pyrrolidin-1-yl-tetrahydro-pyran-3-yl)-4-trifluoromethyl-benzamide;
(−)-2-methoxy-6-methyl-N-4-pyrrolidin-1-yl-tetrahydro-pyran-3-yl)-4-trifluoromethyl-benzamide;
(+)-2-ethyl-6-methoxy-N-4-pyrrolidin-1-yl-tetrahydro-pyran-3-yl)-4-trifluoromethyl-benzamide;
(+2-ethyl-6-methoxy-N-(4-pyrrolidin-1-yl-tetrahydro-pyran-3-yl)-4-trifluoromethyl-benzamide;
(+)-2-cyclopropyl-6-methoxy-N-4-pyrrolidin-1-yl-tetrahydro-pyran-3-yl)-4-trifluoromethyl-benzamide;
(+2-cyclopropyl-6-methoxy-N-4-pyrrolidin-1-yl-tetrahydro-pyran-3-yl)-4-trifluoromethyl-benzamide; and
N-(3SR,4RS)-4-(2-aza-bicyclo[3.1.0]hex-2-yl)-tetrahydro-pyran-3-yl]-2-methoxy-6-methylsulfanyl-4-trifluoromethyl-benzamide.

7. The compound of claim 2, wherein $R^1$ and $R^2$ are each independently hydrogen or $(CR_2)_o$-cycloalkyl, o is 0 or 1 and each R is the same or different and is hydrogen or lower alkyl.

8. The compound of claim 7, selected from the group consisting of
N-((3SR,4RS)-4-cyclopentylamino-tetrahydro-pyran-3-yl)-2-cyclopropyl-4-trifluoromethyl-benzamide;
2-cyclopropyl-N-[(3RS,4SR)-4-(1-cyclopropyl-ethylamino)-tetrahydro-pyran-3-yl]-4-trifluoromethyl-benzamide;
(+)-N-(trans-4-cyclopentylamino-tetrahydro-pyran-3-yl)-2-cyclopropyl-4-trifluoromethyl-benzamide; and
(+)-N-4-cyclohexylamino-tetrahydro-pyran-3-yl)-2-cyclopropyl-4-trifluoromethyl-benzamide.

9. The compound of claim 1, having formula I-2

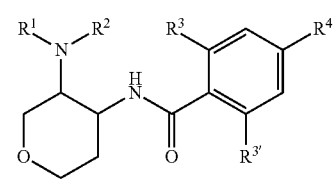

wherein
$R^1$ and $R^2$ are each independently hydrogen, $(CR_2)_o$-cycloalkyl optionally substituted by lower alkyl or hydroxy, or are lower alkyl or heterocycloalkyl,
o is 0 or 1; and
each R is the same or different and is hydrogen or lower alkyl; or
$R^1$ and $R^2$ together with the N atom to which they are attached form a heterocycloalkyl group, selected from the group consisting of pyrrolidinyl, piperidinyl, 3-aza-bicyclo[3.1.0]hex-3-yl and 2-aza-bicyclo[3.1.0]hex-2-yl, each of which is optionally substituted by hydroxy;
$R^3$ is S-lower alkyl, lower alkyl, lower alkoxy or cycloalkyl;
$R^{3'}$ is hydrogen, lower alkyl substituted by halogen, lower alkyl or lower alkoxy; and
$R^4$ is lower alkyl substituted by halogen, lower alkyl or lower alkoxy;
or a pharmaceutically acceptable acid addition salt, racemic mixture, corresponding enantiomer or optical isomer thereof.

10. The compound of claim 9, selected from the group consisting of
cis-2-methoxy-6-methylsulfanyl-N-(3-pyrrolidin-1-yl-tetrahydro-pyran-4-yl)-4-trifluoromethyl-benzamide;
(−)-2-methoxy-6-methylsulfanyl-N-(3-pyrrolidin-1-yl-tetrahydro-pyran-4-yl)-4-trifluoromethyl-benzamide; and
(+)-2-methoxy-6-methylsulfanyl-N-(3-pyrrolidin-1-yl-tetrahydro-pyran-4-yl)-4-trifluoromethyl-benzamide.

11. A pharmaceutical composition comprising a therapeutically effective amount of a compound of formula I

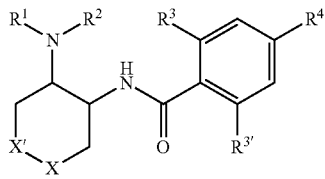

wherein
R¹ and R² are each independently hydrogen, $(CR_2)_o$-cycloalkyl optionally substituted by lower alkyl or hydroxy, or are lower alkyl or heterocycloalkyl,
o is 0 or 1; and
each R is the same or different and is hydrogen or lower alkyl; or
R¹ and R² together with the N atom to which they are attached form a heterocycloalkyl group, selected from the group consisting of pyrrolidinyl, piperidinyl, 3-aza-bicyclo[3.1.0]hex-3-yl and 2-aza-bicyclo[3.1.0]hex-2-yl, each of which is optionally substituted by hydroxy;
R³ is S-lower alkyl, lower alkyl, lower alkoxy or cycloalkyl;
R³' is hydrogen, lower alkyl substituted by halogen, lower alkyl or lower alkoxy;
R⁴ is lower alkyl substituted by halogen, lower alkyl or lower alkoxy;
X is —O— or —CH₂—; and
X' is —O— or —CH₂—; with the proviso that one of X or X' is always —O— and the other is —CH₂—;
or a pharmaceutically acceptable acid addition salt, racemic mixture, corresponding enantiomer or optical isomer thereof and a pharmaceutically acceptable carrier.

12. The composition of claim 11, wherein the compound of formula I, has formula I-1

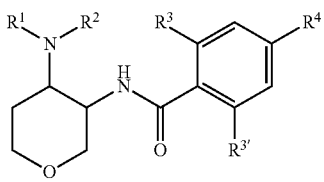

wherein
R¹ and R² are each independently hydrogen, $(CR_2)_o$-cycloalkyl optionally substituted by lower alkyl or hydroxy, or are lower alkyl or heterocycloalkyl,
o is 0 or 1; and
each R is the same or different and is hydrogen or lower alkyl; or
R¹ and R² together with the N atom to which they are attached form a heterocycloalkyl group, selected from the group consisting of pyrrolidinyl, piperidinyl, 3-aza-bicyclo[3.1.0]hex-3-yl and 2-aza-bicyclo[3.1.0]hex-2-yl, each of which is optionally substituted by hydroxy;
R³ is S-lower alkyl, lower alkyl, lower alkoxy or cycloalkyl;
R³' is hydrogen, lower alkyl substituted by halogen, lower alkyl or lower alkoxy; and
R⁴ is lower alkyl substituted by halogen, lower alkyl or lower alkoxy.

13. The composition of claim 11, wherein the compound of formula I, has formula I-2

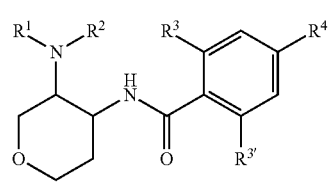

wherein
R¹ and R² are each independently hydrogen, $(CR_2)_o$-cycloalkyl optionally substituted by lower alkyl or hydroxy, or are lower alkyl or heterocycloalkyl,
o is 0 or 1; and
each R is the same or different and is hydrogen or lower alkyl; or
R¹ and R² together with the N atom to which they are attached form a heterocycloalkyl group, selected from the group consisting of pyrrolidinyl, piperidinyl, 3-aza-bicyclo[3.1.0]hex-3-yl and 2-aza-bicyclo[3.1.0]hex-2-yl, each of which is optionally substituted by hydroxy;
R³ is S-lower alkyl, lower alkyl, lower alkoxy or cycloalkyl;
R³' is hydrogen, lower alkyl substituted by halogen, lower alkyl or lower alkoxy; and
R⁴ is lower alkyl substituted by halogen, lower alkyl or lower alkoxy.

* * * * *